US008058294B2

(12) United States Patent
Whittock et al.

(10) Patent No.: US 8,058,294 B2
(45) Date of Patent: *Nov. 15, 2011

(54) PHARMACEUTICAL SALTS OF N-[2-(DIETHYLAMINO)ETHYL]-N-(2-{[2-(4-HYDROXY-2-OXO-2,3-DIHYDRO-1,3-BENZOTHIAZOL-7-YL)ETHYL]AMINO}ETHYL)-3-[2-(1-NAPTHYL)ETHOXY]PROPANAMIDE

(75) Inventors: Robert Whittock, Leicestershire (GB); Jane Withnall, Leicestershire (GB)

(73) Assignee: AstraZeneca AB, Sodertalje (SE)

( * ) Notice: Subject to any disclaimer, the term of this patent is extended or adjusted under 35 U.S.C. 154(b) by 383 days.

This patent is subject to a terminal disclaimer.

(21) Appl. No.: 12/069,180

(22) Filed: Feb. 7, 2008

(65) Prior Publication Data

US 2008/0249145 A1    Oct. 9, 2008

(30) Foreign Application Priority Data

Feb. 8, 2007  (GB) .................................. 0702458.1

(51) Int. Cl.
A61K 31/428     (2006.01)
C07D 277/68     (2006.01)

(52) U.S. Cl. ......................................... 514/367; 548/165

(58) Field of Classification Search .................. 548/165, 548/169; 514/367
See application file for complete search history.

(56) References Cited

U.S. PATENT DOCUMENTS

| 2,653,977 | A | 9/1953 | Craig et al. |
| 3,775,477 | A | 11/1973 | Diana |
| 4,460,581 | A | 7/1984 | Schromm et al. |
| 5,648,370 | A | 7/1997 | Bonnert et al. |
| 6,686,353 | B1 | 2/2004 | Shiota et al. |
| 7,700,782 | B2 | 4/2010 | Connolly et al. |
| 7,709,511 | B2 | 5/2010 | Bonnert et al. |
| 2002/0055651 | A1 | 5/2002 | Moran et al. |
| 2003/0229058 | A1 | 12/2003 | Moran et al. |
| 2006/0106075 | A1 | 5/2006 | Cuenoud et al. |
| 2008/0207698 | A1 | 8/2008 | Connolly et al. |
| 2008/0242649 | A1 | 10/2008 | Cadogan et al. |
| 2008/0249145 | A1 | 10/2008 | Whittock et al. |
| 2008/0300275 | A1 | 12/2008 | Bonnert et al. |
| 2009/0029958 | A1 | 1/2009 | Alcaraz et al. |
| 2009/0062259 | A1 | 3/2009 | Alcaraz et al. |
| 2009/0203753 | A1 | 8/2009 | Bailey et al. |
| 2009/0221653 | A1 | 9/2009 | Bailey et al. |
| 2010/0022491 | A1 | 1/2010 | Connolly et al. |
| 2010/0210688 | A1 | 8/2010 | Bonnert et al. |
| 2010/0249200 | A1 | 9/2010 | Connolly et al. |

FOREIGN PATENT DOCUMENTS

| EP | 0162576 | 11/1985 |
| EP | 0174811 | 3/1986 |
| EP | 0175525 | 3/1986 |
| EP | 0220878 | 5/1987 |
| EP | 0303466 | 2/1989 |
| EP | 0422889 | 4/1991 |
| JP | 2005-187357 | 7/2005 |
| SE | 7415945 | 6/1975 |
| WO | WO 92/08708 | 5/1992 |
| WO | WO 93/23385 | 11/1993 |
| WO | WO 93/24473 | 12/1993 |
| WO | WO 97/10227 | 3/1997 |
| WO | WO 97/23470 | 7/1997 |
| WO | WO 97/44329 | 11/1997 |
| WO | WO 98/38180 | 9/1998 |
| WO | WO 98/45294 | 10/1998 |
| WO | WO 99/36095 | 7/1999 |
| WO | WO 99/64035 | 12/1999 |
| WO | WO 00/75114 | 12/2000 |
| WO | WO 01/11933 | 2/2001 |
| WO | WO 01/12167 | 2/2001 |
| WO | WO 01/12191 | 2/2001 |
| WO | WO 01/12192 | 2/2001 |
| WO | WO 01/42193 | 6/2001 |
| WO | WO 02/06255 | 1/2002 |
| WO | WO 02/076933 | 10/2002 |
| WO | WO 03/024439 | 3/2003 |
| WO | WO 2004/016578 | 2/2004 |
| WO | WO 2004/016601 | 2/2004 |
| WO | WO 2004/039766 | 5/2004 |
| WO | WO 2004/071388 | 8/2004 |
| WO | WO 2004/074276 | 9/2004 |
| WO | WO 2004/089892 | 10/2004 |
| WO | WO 2005/030678 | 4/2005 |
| WO | WO 2005/040103 | 5/2005 |
| WO | WO 2005/044787 | 5/2005 |
| WO | WO 2005/070872 | 8/2005 |
| WO | WO 2005/074924 | 8/2005 |
| WO | WO 2005/092841 | 10/2005 |
| WO | WO 2005/092861 | 10/2005 |
| WO | WO 2005/092870 | 10/2005 |
| WO | WO 2005/110990 | 11/2005 |

(Continued)

OTHER PUBLICATIONS

M. Johnson Paediatric Respiratory Reviews 2001, 2, 57-62.* Schafer et al. (Drug Discovery Today 2008, 13 (21/22), 913-916).*
Horig et al. Journal of Translational Medicine 2004, 2(44).*
Austin et al. "QSAR and the Rational Design of Long-Acting Dual $D_2$-Receptor/$\beta_2$-Adrenoceptor Agonists" J. Med. Chem. 2003 46:3210-3220.
Berge et al. "Pharmaceutical Salts" J Pharmaceutical Sciences. 1977 66(1) 1-19.
Bonnert et al. "Dual $D_2$-Receptor and $\beta_2$-Adrenoceptor Agonists for the Treatment of Airway Diseases. 1. Discovery and Biological Evaluation of Some 7-(2-Aminoethyl)-4-hydroxybenzothiazol-2(3H)-one Analogues" J Med Chem. 1998 (41) 4915-4917.
Davies et al. "Indacaterol. Asthma Therapy Treatment of COPD $\beta_2$-Adrenoceptor Agonist" Drugs of the Future. 2005 30(12) 1219-1224.
Dougall et al. "Dual dopamine $D_2$ receptor and $\beta_2$-adrenoceptor agonists for the treatment of chronic obstructive pulmonary disease: the pre-clinical rationale" Respir Med (Suppl A). 2003 (97) S3-S7 (Abstract).

(Continued)

Primary Examiner — Jason M Nolan
(74) Attorney, Agent, or Firm — Fish & Richardson P.C.

(57) ABSTRACT

A pharmaceutically acceptable salt of N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide provided it is not the dihydrobromide or dihydrochloride salt; and the use of such a compound as a medicament (for example in the treatment of respiratory diseases (such as asthma or COPD).

5 Claims, 13 Drawing Sheets

FOREIGN PATENT DOCUMENTS

| | | |
|---|---|---|
| WO | WO 2005/111002 | 11/2005 |
| WO | WO 2005/111004 | 11/2005 |
| WO | WO 2005/121065 | 12/2005 |
| WO | WO 2006/014704 | 2/2006 |
| WO | WO 2006/023457 | 3/2006 |
| WO | WO 2006/023460 | 3/2006 |
| WO | WO 2006/031556 | 3/2006 |
| WO | WO 2006/056471 | 6/2006 |
| WO | WO 2006/074897 | 7/2006 |
| WO | WO 2006/128675 | 12/2006 |
| WO | WO 2007/010356 | 1/2007 |
| WO | WO 2007/018461 | 2/2007 |
| WO | WO 2007018461 A1 * | 2/2007 |
| WO | WO 2007/027133 | 3/2007 |
| WO | WO 2007/027134 | 3/2007 |
| WO | WO 2007/102771 | 9/2007 |
| WO | WO 2007/106016 | 9/2007 |
| WO | WO 2008/041914 | 4/2008 |
| WO | WO 2008/075025 | 6/2008 |
| WO | WO 2008/075026 | 6/2008 |
| WO | WO 2008/096111 | 8/2008 |
| WO | WO 2008/096112 | 8/2008 |
| WO | WO 2008/096119 | 8/2008 |
| WO | WO 2008/096121 | 8/2008 |
| WO | WO 2008/104776 | 9/2008 |
| WO | WO 2008/104790 | 9/2008 |
| WO | WO 2009/037503 | 3/2009 |

OTHER PUBLICATIONS

Fernández et al. "Alkaline Hydrolysis of 1,2,3-Trisubstituted Cyclic Amidinium Salts. Kinetic Study of N 4 N' Acyl Migration in Alkaline Solution in an Ethylenediamine Derivative" J.C.S. Perkin II. 1978 545-550.

Fernández et al. "N 4 N' Intramolecular Acyl Transfer in Acid Media for Alkylenediamine Derivatives" J.C.S. Perkin II. 1978 550-553.

Norman, "Which of three structures is AZD-3199? WO-2008104790, WO-2008096112 and WO-2008096119" Expert Opin. Ther. Patents. 2009 19(7) 1-7.

Weinstock et al. "Synthesis and Evaluation of Non-Catechol D-1 and D-2 Dopamine Receptor Agonists: Benzimidazol-2-one, Benzoxazol-2-one, and the Highly Potent Benzothiazol-2-one 7 Ethylamines" J Med Chem. 1987 (30) 1166-1176.

Wermuth et al., Handbook of Pharmaceutical salts: properties, selection and use, (2002) pp. 1-7: published by Wiley-VCH Verlag, ISBN: 10-3-906390-26-8.

Wright et al. "The Rearrangement of N-(Methylaminoalkyl)anilides" J Org Chem. 1961 26(6) 2120-2123.

USPTO Non-Final Office Action in U.S. Appl. No. 11/959,679, mailed Feb. 25, 2009, 12 pages.

Fish & Richardson P.C., Amendment in Reply to Action of Feb. 25, 2009 in U.S. Appl. No. 11/959,679, filed Jul. 15, 2009, 6 pages.

USPTO Notice of Allowance in U.S. Appl. No. 11/959,679, mailed Nov. 9, 2009, 9 pages.

Fish & Richardson P.C., Response to Notice of Allowance mailed Nov. 9, 2009 in U.S. Appl. No. 11/959,679, filed Feb. 9, 2009, 2 pages.

USPTO Notice of Allowance in U.S. Appl. No. 12/063,322, mailed Feb. 26, 2010, 12 pages.

Fish & Richardson P.C., Response to Notice of Allowance mailed Feb. 26, 2010 in U.S. Appl. No. 12/063,322, filed Mar. 5, 2010, 2 pages.

USPTO Notice of Allowance in U.S. Appl. No. 12/065,160, mailed Jun. 15, 2010, 9 pages.

Chanez et al. "Corticosteroid reversibility in COPD is related to features of asthma" Am. J. Respir. Crit. Care Med. 1997 155(5) 1529-1534 (abstract only).

USPTO Non-Final Office Action in U.S. Appl. No. 12/027,424, mailed Mar. 8, 2011, 12 pages.

Fish & Richardson P.C., RCE/IDS in response to Notice of Allowance mailed Jun. 15, 2010 in U.S. Appl. No. 12/065,160, filed Sep. 15, 2010, 9 pages.

USPTO Non-Final Office Action in U.S. Appl. No. 12/282,634, mailed Aug. 5, 2010, 13 pages.

Fish & Richardson P.C., Amendment in Reply to Action of Aug. 5, 2010 in U.S. Appl. No. 12/282,634, filed Nov. 5, 2010, 18 pages.

USPTO Notice of Allowance in U.S. Appl. No. 12/282,634, mailed Jan. 24, 2011, 12 pages.

Swedish Search Report for Application No. PCT/SE2006/000927, dated Oct. 27, 2006, 8 pages.

European Search Report for Application No. PCT/GB2007/004861, dated Mar. 28, 2008, 4 pages.

* cited by examiner

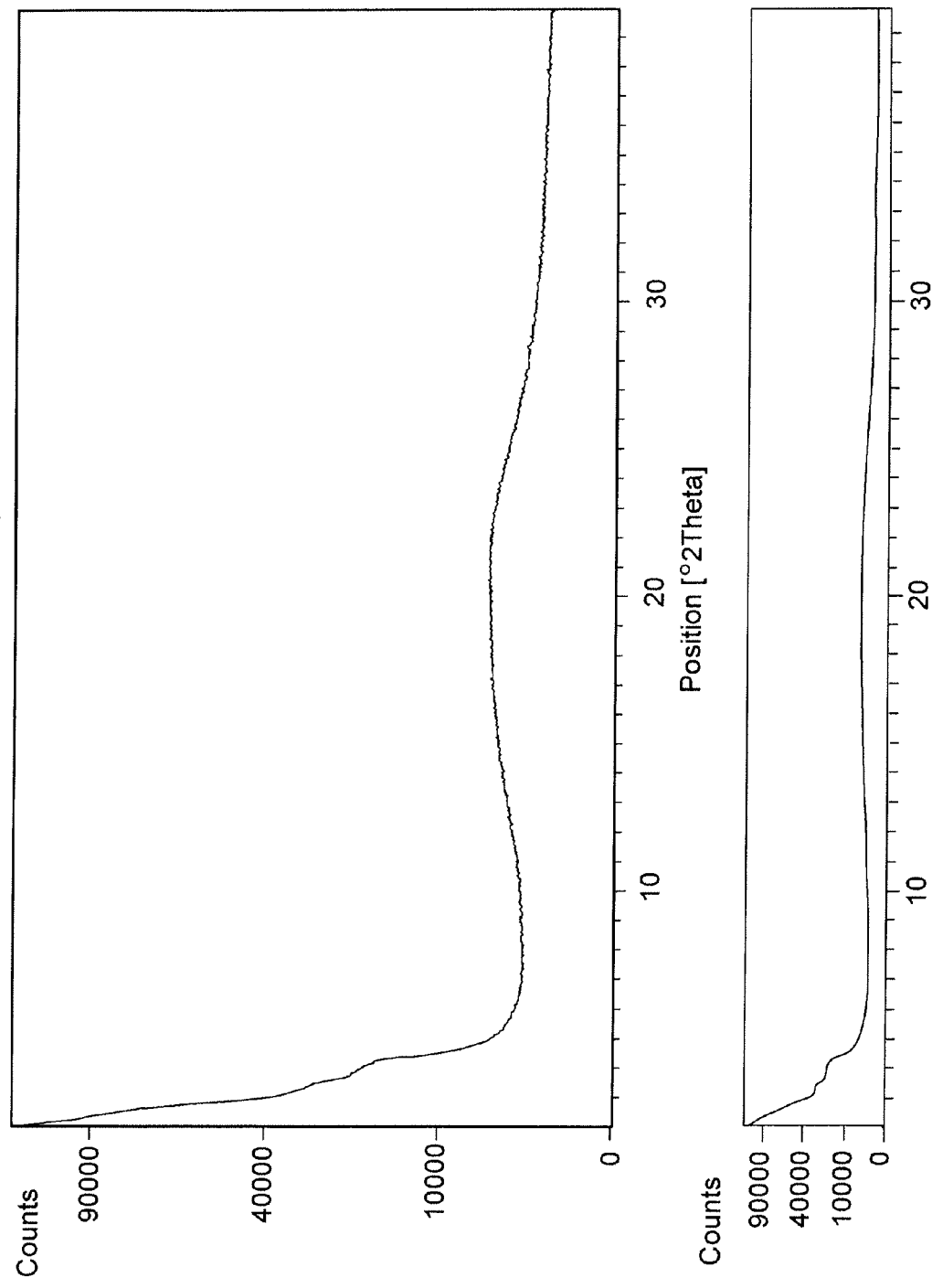
FIG. 1 XRPD of Amorphous form of Compound B

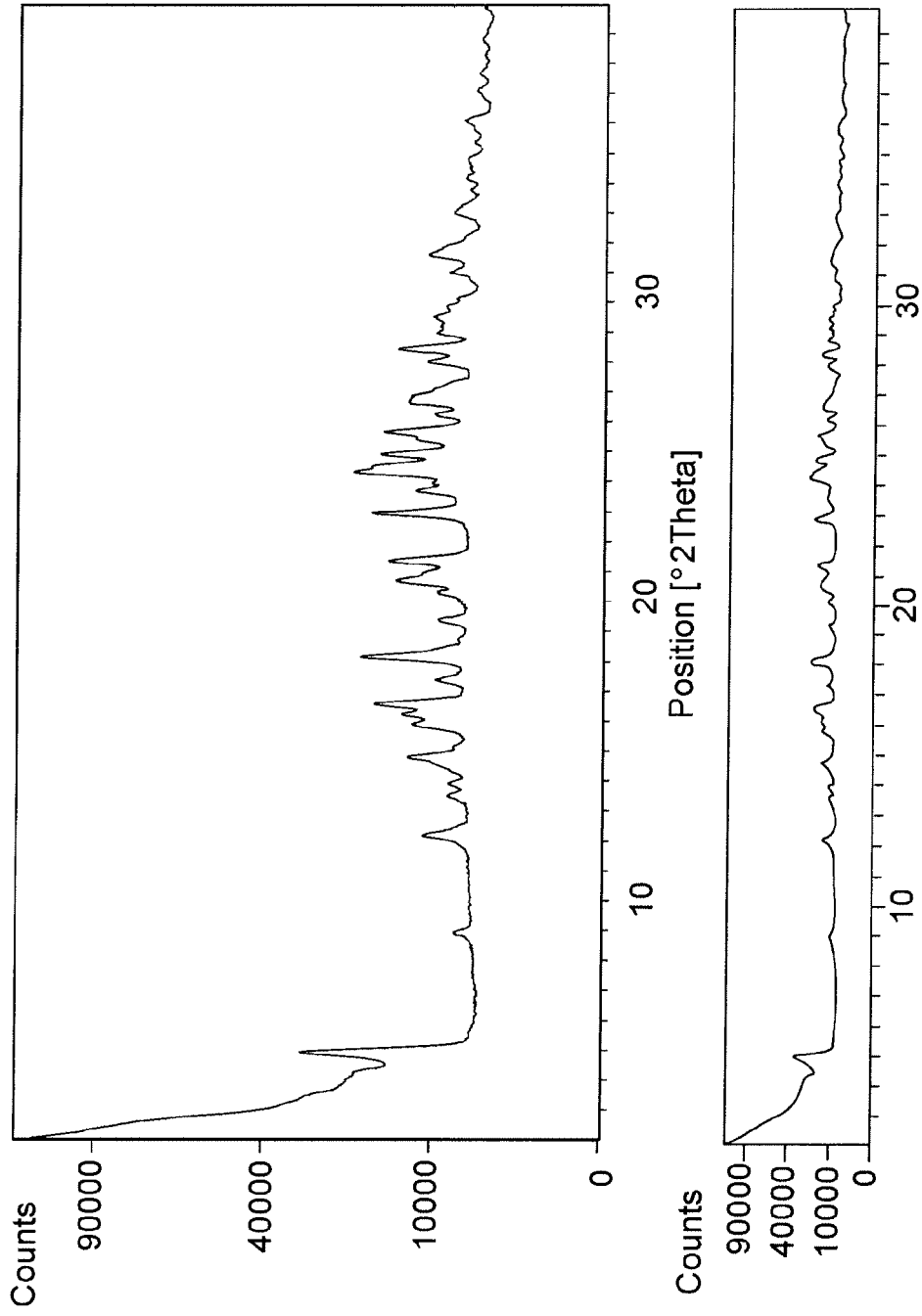
FIG. 2  XRPD of Polymorph A of Compound A

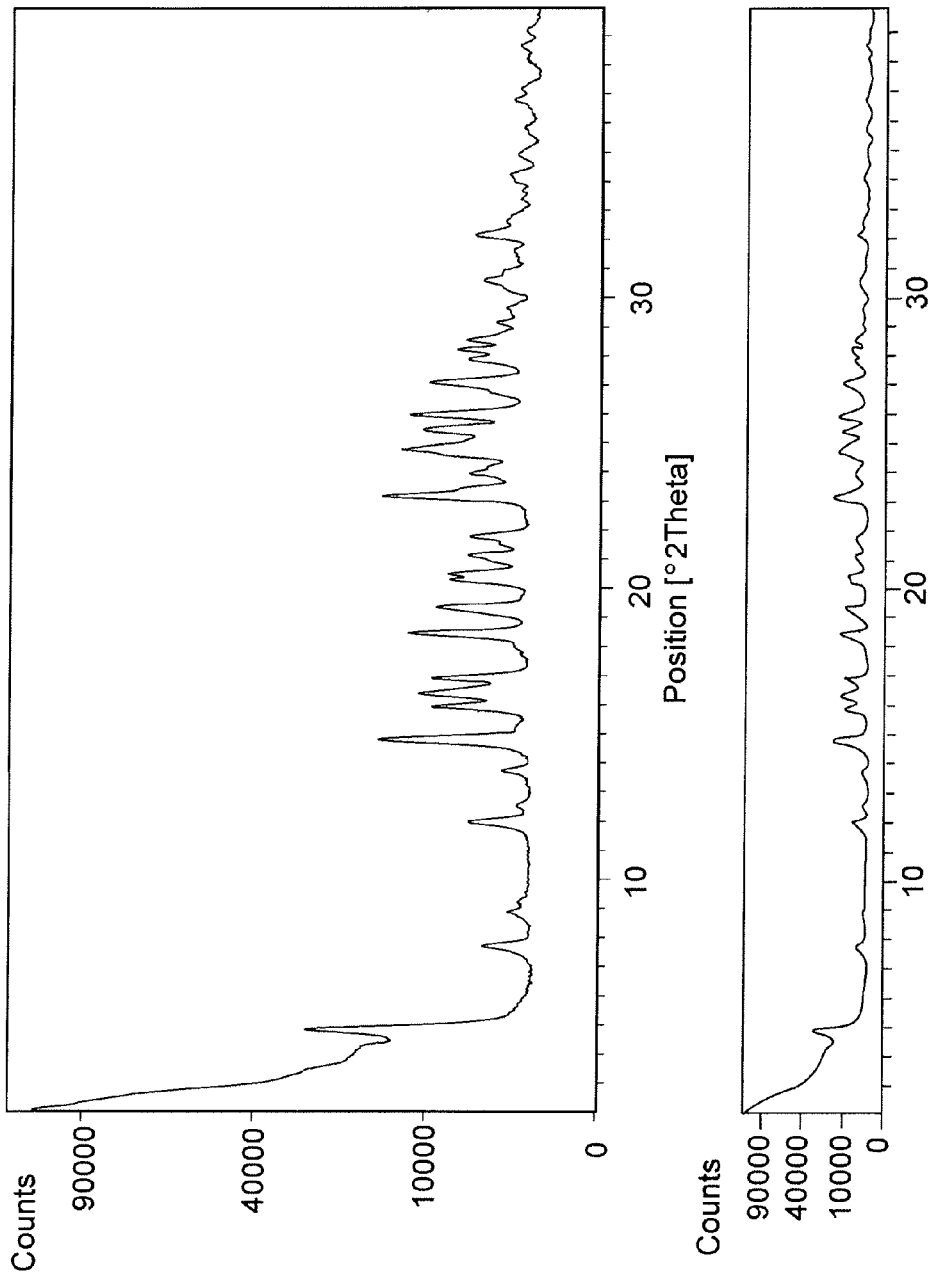

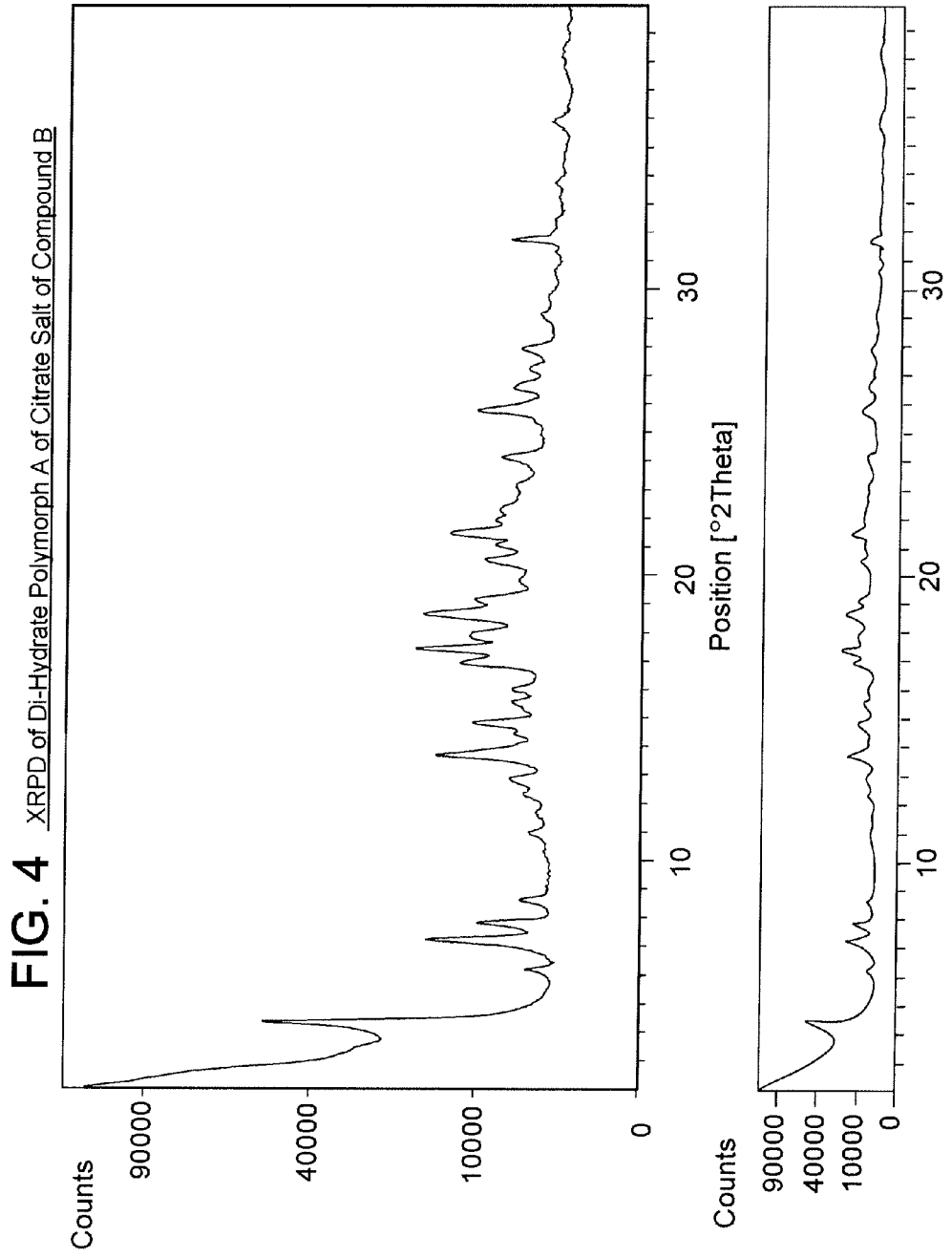
FIG. 4  XRPD of Di-Hydrate Polymorph A of Citrate Salt of Compound B

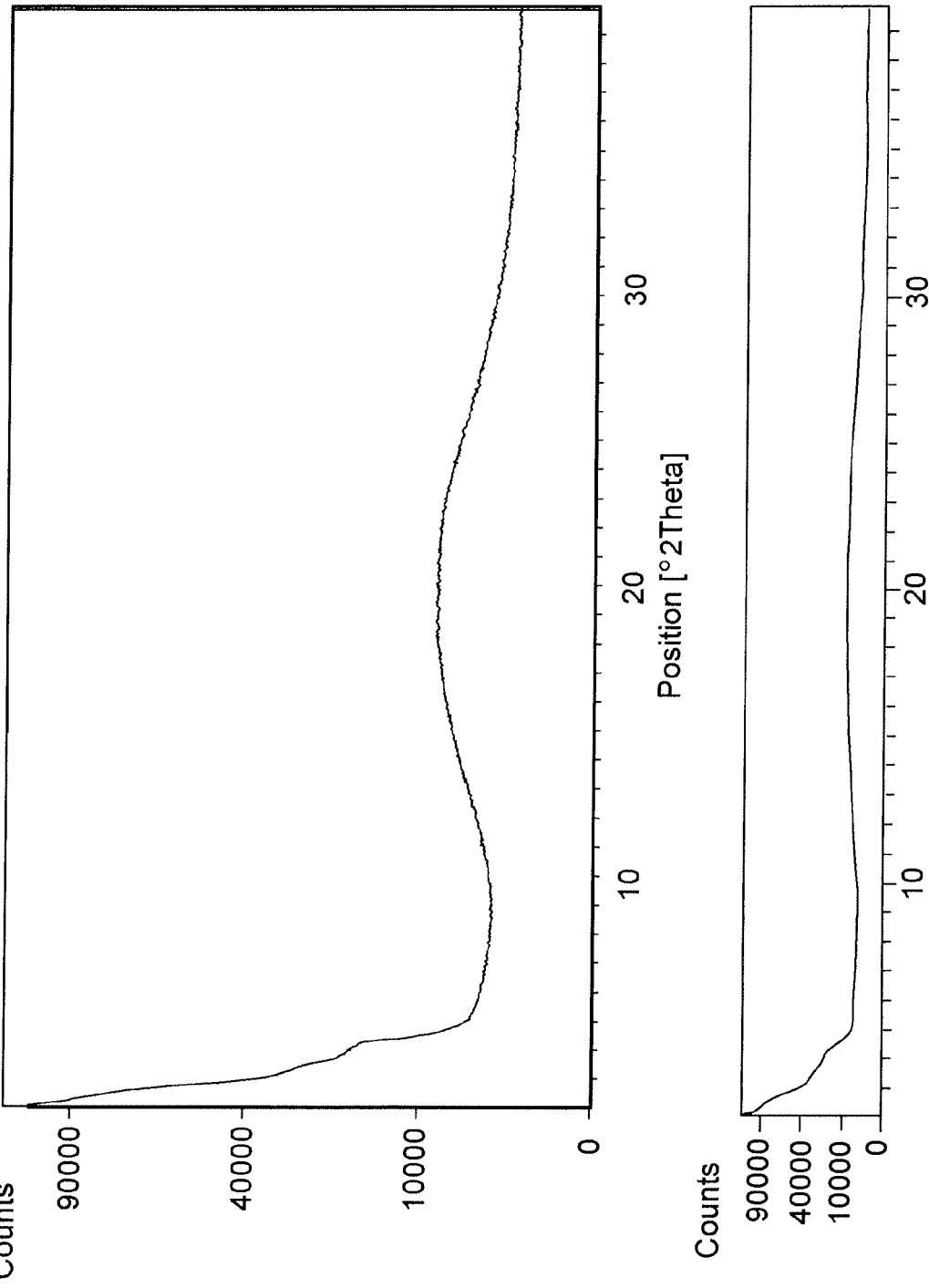
FIG. 5  XRPD of Amorphous form of Di-Tosylate Salt of Compound B

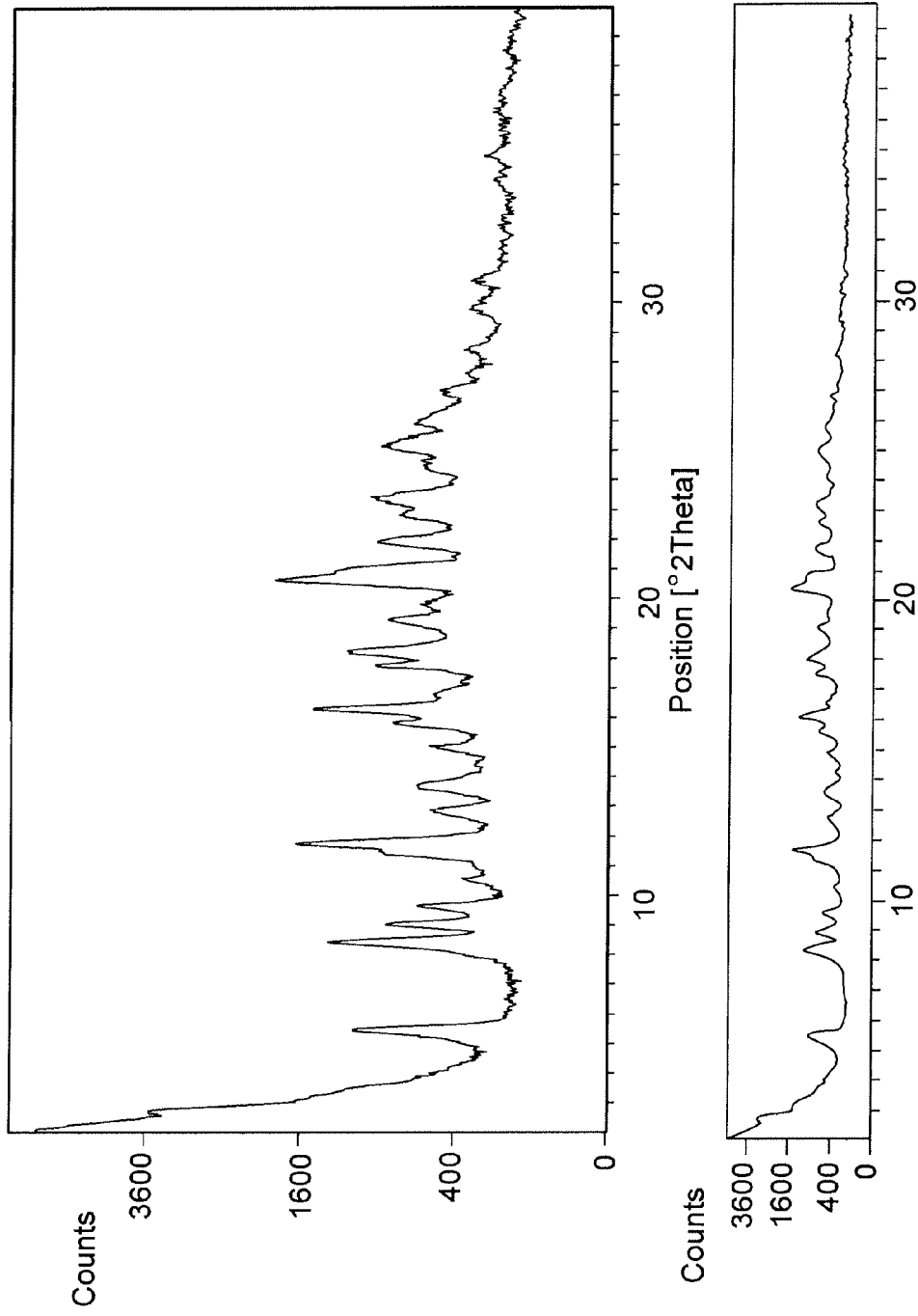
FIG. 6  XRPD of Di-Hemi-Hydrate Polymorph A of Phosphate Salt of Compound B

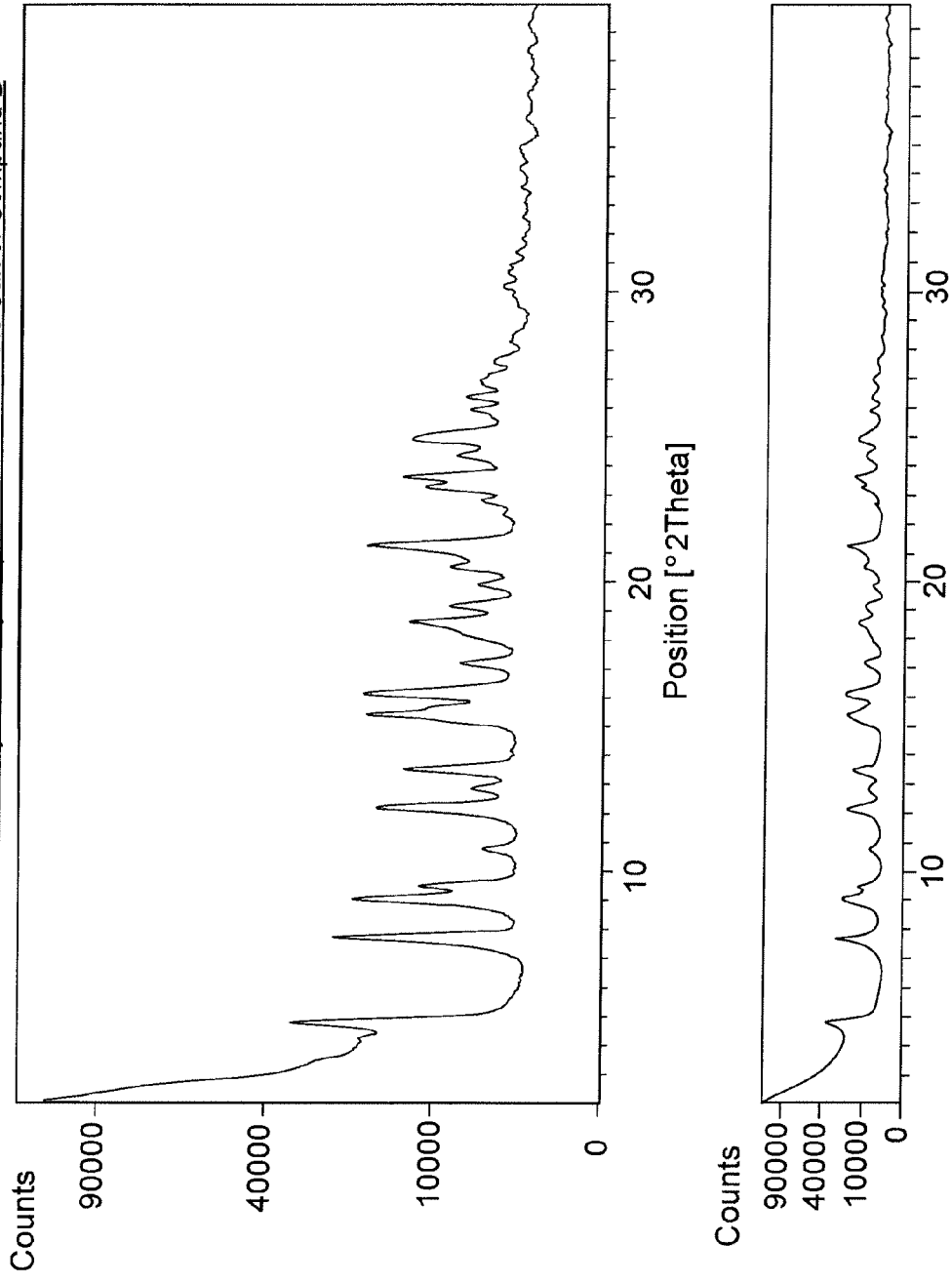
FIG. 7  XRPD of Di-Hydrate Polymorph A of Di-Xinafoate Salt of Compund B

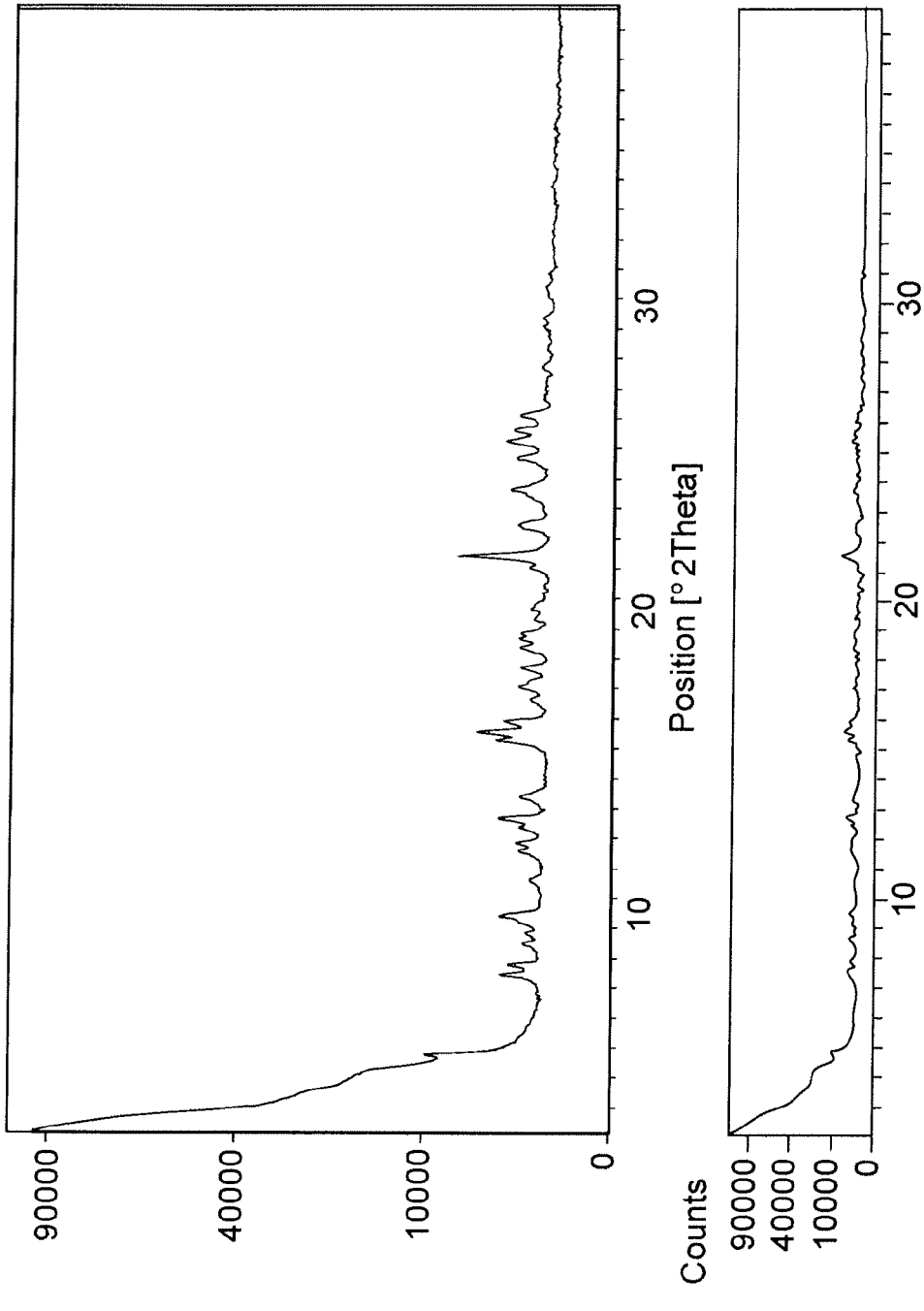
FIG. 8  XRPD of Di-Hemi-Hydrate Polymorph A of Di-Xinafoate Salt of Compound B

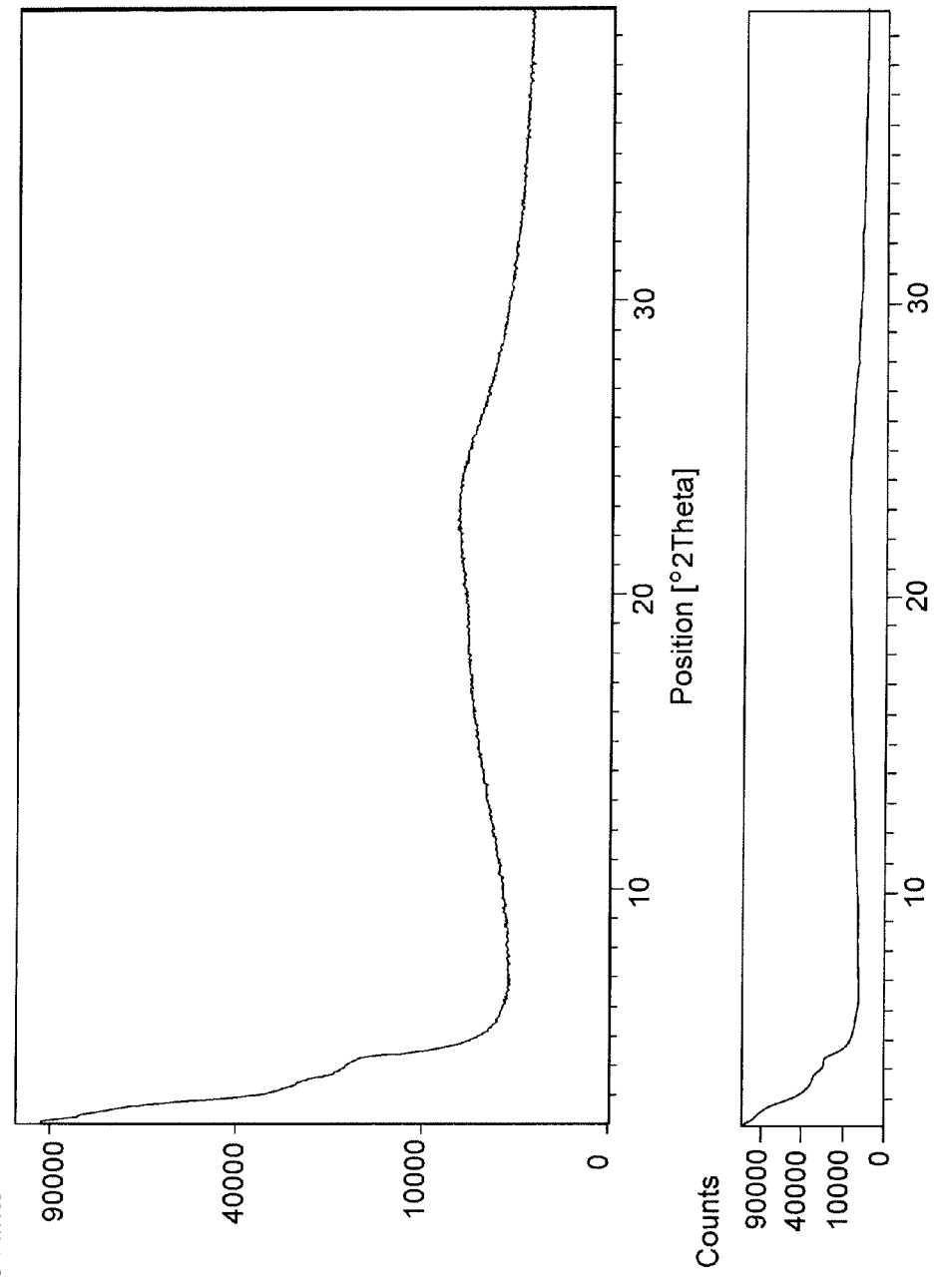

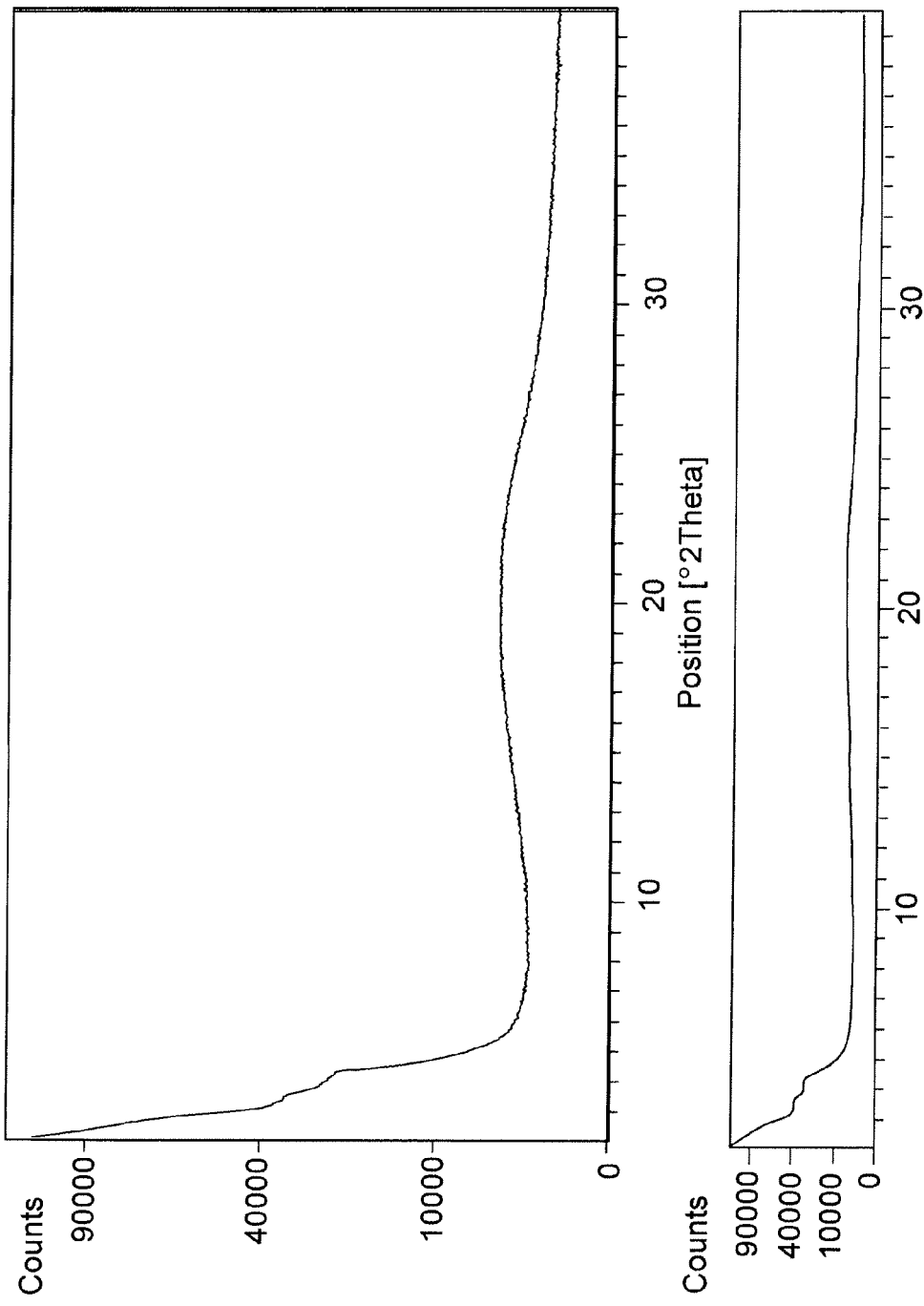
FIG. 10  XRPD of Amorphous form of Mono Benzoate of Compound B

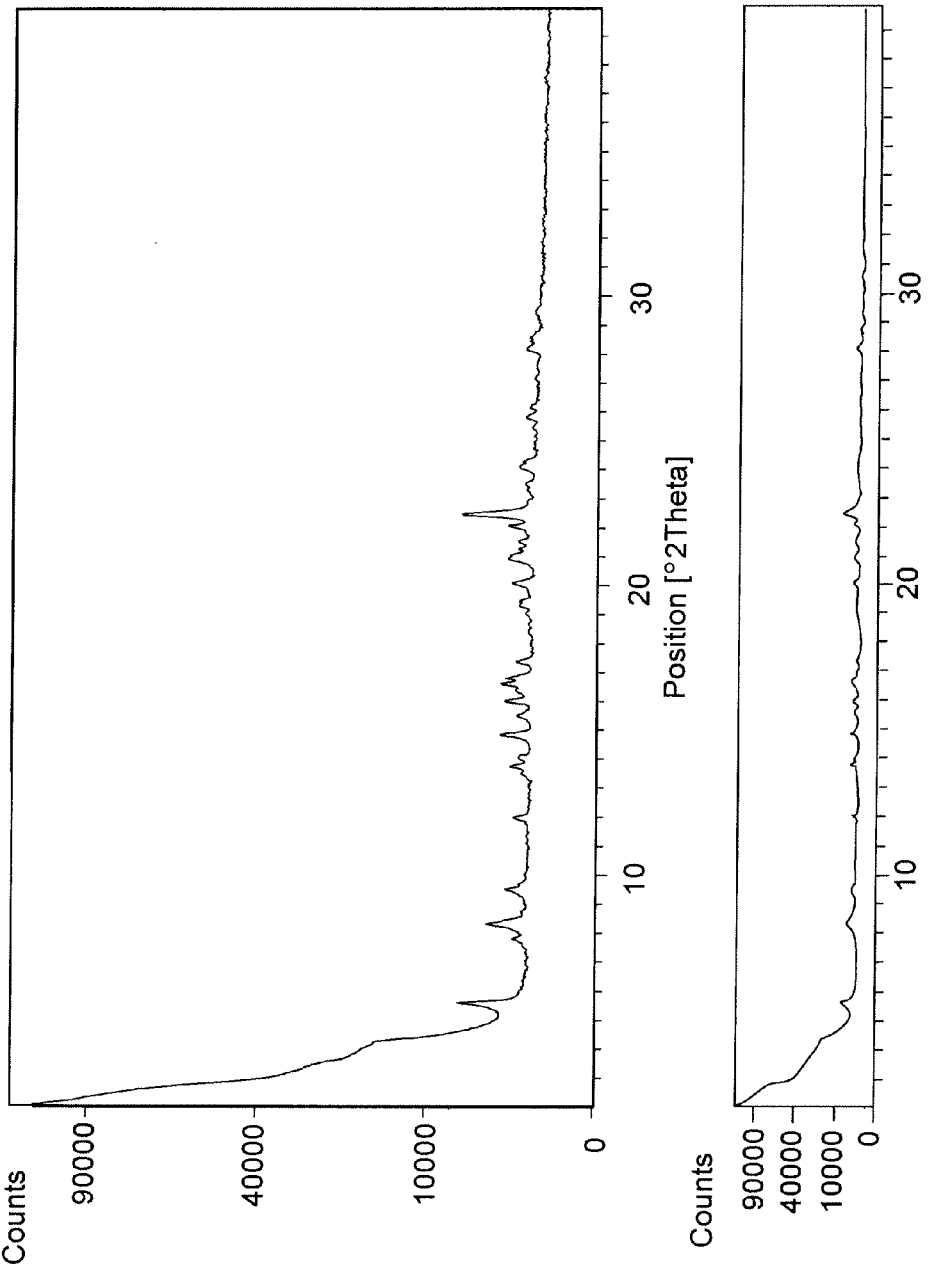
FIG. 11  XRPD of Crystalline form of Mono Benzoate of Compound B

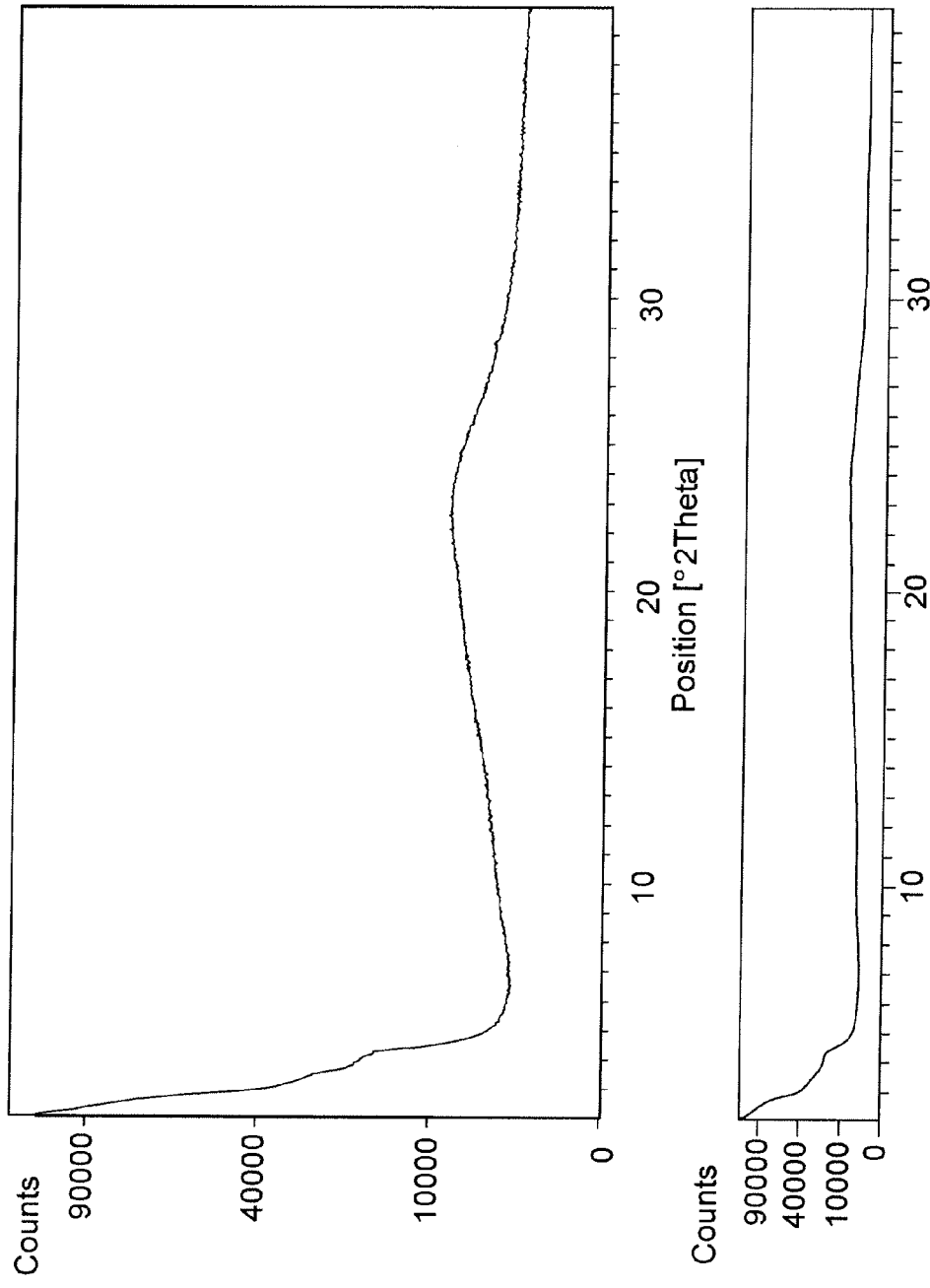
FIG. 12  XRPD of Amorphous form of Mono Fumarate Salt of Compound B

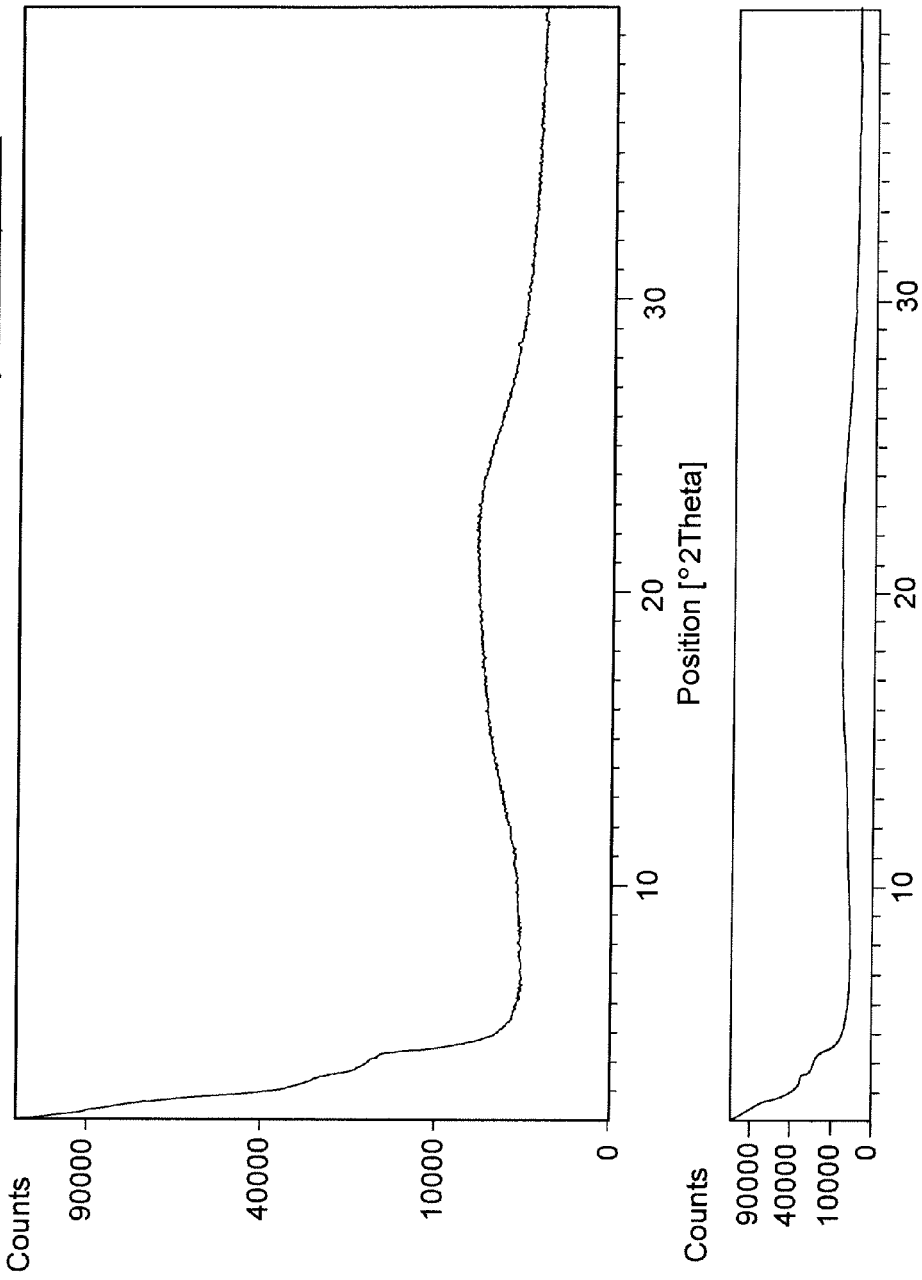
FIG. 13  XRPD of Amorphous form of Mono Besylate of Compound B

PHARMACEUTICAL SALTS OF N-[2-(DIETHYLAMINO)ETHYL]-N-(2-{[2-(4-HYDROXY-2-OXO-2,3-DIHYDRO-1,3-BENZOTHIAZOL-7-YL)ETHYL]AMINO} ETHYL)-3-[2-(1-NAPTHYL)ETHOXY] PROPANAMIDE

CROSS REFERENCE TO RELATED APPLICATIONS

This application claims the benefit of Great Britain Application No.: GB 0702458.1, filed on Feb. 8, 2007, which is incorporated herein by reference in its entirety.

TECHNICAL FIELD

The present invention concerns new salt forms of N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide, compositions comprising such new salt forms, processes for preparing such salt forms, and the use of such salt forms in the treatment of disease states (such as respiratory disease states, for example asthma or COPD).

BACKGROUND

N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide free base and its dihydrobromide and dihydrochloride salts are β2 adrenoceptor agonists and are disclosed in PCT/SE2006/000927 (published as WO 2007/018461, see Examples 7, 15 and 16). These compounds show at least 10-fold selectivity for β2 adrenoceptor over adrenergic α1D, adrenergic β1 and dopamine D2.

SUMMARY

The present invention provides a pharmaceutically acceptable salt of N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide provided it is not the dihydrobromide or dihydrochloride salt.

A pharmaceutically acceptable salt includes for example, a trifluoroacetate, sulphate, phosphate, acetate, fumarate, maleate, citrate, pyruvate, succinate, oxalate, methanesulphonate, p-toluenesulphonate, bisulphate, benzenesulphonate, ethanesulphonate, malonate, xinafoate, ascorbate, oleate, nicotinate, saccharinate, adipate, formate, glycolate, L-lactate, D-lactate, aspartate, malate, L-tartrate, D-tartrate, stearate, 2-furoate, 3-furoate, napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), 2-mesitylenesulphonate or 2-naphthalenesulphonate. A suitable salt can also be D-mandelate or L-mandelate.

A salt of the invention can exist as a solvate (such as a hydrate), and the present invention covers all such solvents.

In one particular aspect the present invention provides a pharmaceutically acceptable salt of N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide which is a citrate, ditosylate, phosphate, dixinafoate, sulphate, mono-benzoate, fumarate or besylate salt.

In a further aspect the present invention provides a mono-citrate salt of N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide.

In a still further aspect the present invention provides a citrate salt of N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide having an X-ray powder diffraction (XRPD) pattern containing specific peaks at: 4.4 (±0.1°), 7.2 (±0.1°), 13.7 (±0.1°), 17.4 (±0.1°), 18.7 (±0.1°) and 21.4 (±0.1°) 2θ.

A citrate salt can be prepared by adding citric acid to a solution of N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide in a suitable aliphatic alcohol (such as methanol), solubilising all material (at elevated temperature if necessary), allowing the solution to cool, whereupon the citrate salt precipitates from the solution and can be collected.

In another aspect the present invention provides a dixinafoate salt of N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide.

In yet another aspect the present invention provides a dixinafoate salt of N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide as a di-hydrate having an X-ray powder diffraction pattern containing specific peaks at: 4.8 (±0.1°), 7.7 (±0.1°), 9.1 (±0.1°), 12.2 (±0.1°), 16.1 (±0.1°) and 21.3 (±0.1°) 2θ.

In a further aspect the present invention provides a dixinafoate salt of N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide as a D1-Hemi-Hydrate having an X-ray powder diffraction pattern containing specific peaks at: 8.5 (±0.1°), 9.4 (±0.1°), 11.6 (±0.1°), 11.9 (±0.1°), 16.6 (±0.1°), 17.7 (±0.1°) and 22.4 (±0.1°) 2θ.

A xinafoate salt can be prepared by adding 1-hydroxy-2-naphthoic acid to a solution of N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide in a suitable aliphatic alcohol (such as methanol), mixing at elevated temperature (such as reflux), and allowing to cool, whereupon the xinafoate salt can be collected.

In another aspect the present invention provides a phosphate salt of N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide.

In yet another aspect the present invention provides a phosphate salt of N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide as a di-hemi-hydrate having an X-ray powder diffraction pattern containing specific peaks at: 5.5 (±0.1°), 8.4 (±0.1°), 9.04 (±0.1°), 11.8 (±0.1°), 16.3 (±0.1°) and 20.6 (0.1°) 2θ.

A phosphate salt can be prepared by adding phosphoric acid to a solution of N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide in a suitable aliphatic alcohol (such as methanol), mixing at elevated temperature (such as reflux), and allowing to cool, whereupon the phosphate salt can be collected.

In another aspect the present invention provides a mono-benzoate salt of N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide.

In yet another aspect the present invention provides a crystalline form of the mono-benzoate salt of N-[2-(Diethylamino)ethyl]-N-(2-[2-(4-hydroxy-2-oxo-2,3-dihydro-1,3- benzothiazol-7-yl)ethyl]amino}ethyl)-3-[2-(1-naphthyl) ethoxy]propanamide having an X-ray powder diffraction pattern containing specific peaks at: 5.6 (±0.1°), 8.3 (±0.1°), 9.5 (±0.1°), 14.8 (±0.1°), 20.1 (±0.1°) and 22.5 (±0.1°) 2θ.

A benzoate salt can be prepared by adding benzoic acid to a solution of N-[2-(Diethylamino)ethyl]-N-(2-{[2-(4-hydroxy-2-oxo-2,3-dihydro-1,3-benzothiazol-7-yl)ethyl] amino}ethyl)-3-[2-(1-naphthyl)ethoxy]propanamide in a suitable aliphatic alcohol (such as methanol), mixing (for example at room temperature (such as 10-30° C.)) and then collecting the benzoate salt.

The salts of the present invention can be prepared by using or adapting: the methods presented above; the methods presented in the Preparations or Examples below; or, the methods described in the literature.

The salts of the invention can be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) or adenovirus; or eosinophilic esophagitis;

2. bone and joints: arthritides associated with or including osteoarthritis/osteoarthrosis, both primary and secondary to, for example, congenital hip dysplasia; cervical and lumbar spondylitis, and low back and neck pain; osteoarthritis; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthritides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, is eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 15. gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

Thus, the present invention provides a salt as hereinbefore defined for use in therapy.

In a further aspect, the present invention provides the use of a salt as hereinbefore defined in the manufacture of a medicament for use in therapy (for example a respiratory disease state)

In a still further aspect the present invention provides a salt as hereinbefore described for the treatment of a respiratory disease state.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention still further provides a method of treating, or reducing the risk of, an inflammatory disease or condition (including a reversible obstructive airways disease or condition) which comprises administering to a patient in need thereof a therapeutically effective amount of a salt as hereinbefore defined.

In particular, a salt of the present invention may be used in the treatment of adult respiratory distress syndrome (ARDS), pulmonary emphysema, bronchitis, bronchiectasis, chronic obstructive pulmonary disease (COPD), asthma and rhinitis.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (µg/kg) to 100 micrograms per kilogram body weight (µg/kg). Alternatively, if the compound is administered orally, then the daily dosage of the compound of the invention may be in the range from 0.01 micrograms per kilogram body weight (µg/kg) to 100 milligrams per kilogram body weight (mg/kg).

A salt of the invention may be used on its own but will generally be administered in the form of a pharmaceutical composition in which a salt of the invention (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will for example comprise from 0.05 to 99% w (percent by weight), such as from 0.05 to 80% w, for example from 0.10 to 70% w, and such as from 0.10 to 50% w, of active ingredient, all percentages by weight being based on total composition.

The present invention also provides a pharmaceutical composition comprising a salt as hereinbefore defined, in association with a pharmaceutically acceptable adjuvant, diluent or carrier.

The invention further provides a process for the preparation of a pharmaceutical composition of the invention which comprises mixing a salt as hereinbefore defined with a pharmaceutically acceptable adjuvant, diluent or carrier.

BRIEF DESCRIPTION OF THE DRAWINGS

FIG. 1 shows the XRPD of Amorphous form of Compound B.

FIG. 2 shows the XRPD of Polymorph A of Compound A.

FIG. 3 shows the XRPD of Polymorph A of dihydrochloride salt of Compound B.

FIG. 4 shows the XRPD of Di-Hydrate Polymorph A of Citrate Salt of Compound B.

FIG. 5 shows the XRPD of Amorphous form of Di-Tosylate Salt of Compound B.

FIG. 6 shows the XRPD of Di-Hemi-Hydrate Polymorph A of Phosphate Salt of Compound B.

FIG. 7 shows the XRPD of Di-Hydrate Polymorph A of Di-Xinafoate Salt of Compound B.

FIG. 8 shows the XRPD of Di-Hemi-Hydrate Polymorph A of Di-Xinafoate Salt of Compound B.

FIG. 9 shows the XRPD of Amorphous form of Sulphate Salt of Compound B.

FIG. 10 shows the XRPD of Amorphous form of Mono Benzoate of Compound B.

FIG. 11 shows the XRPD of Crystalline form of Mono Benzoate of Compound B.

FIG. 12 shows the XRPD of Amorphous form of Mono Fumarate Salt of Compound B.

FIG. 13 shows the XRPD of Amorphous form of Mono Besylate of Compound B.

DETAILED DESCRIPTION

A pharmaceutical composition of the invention can be administered topically (e.g. to the skin or to the lung and/or airways) in the form, e.g., of a cream, solution, suspension, heptafluoroalkane (HFA) aerosol or dry powder formulation, for example, a formulation in the inhaler device known as the Turbuhaler®; or systemically, e.g. by oral administration in the form of a tablet, capsule, syrup, powder or granule; or by parenteral administration in the form of a solution or suspension; or by subcutaneous administration; or by rectal administration in the form of a suppository; or transdermally.

A dry powder formulation or pressurized HFA aerosol of a salt of the invention may be administered by oral or nasal inhalation. For inhalation, the salt is desirably finely divided. The finely divided compound has, for example, a mass median diameter of less than 10 μM, and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

A salt of the invention may also be administered by means of a dry powder inhaler. The inhaler may be a single or a multi dose inhaler, and may be a breath actuated dry powder inhaler.

One possibility is to mix the finely divided compound of the invention with a carrier substance, for example, a mono-, di- or polysaccharide, a sugar alcohol, or another polyol. A suitable carrier is, for example, a sugar, for example, lactose, glucose, raffinose, melezitose, lactitol, maltitol, trehalose, sucrose, mannitol; or starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the above-mentioned excipients for tablets. Also liquid or semisolid formulations of the compound of the invention may be filled into hard gelatine capsules.

A liquid preparation for oral application may be in the form of a syrup or suspension, for example, a solution containing a salt of the invention, the balance being sugar and a mixture of ethanol, water, glycerol and propylene glycol. Optionally such a liquid preparation may contain a colouring agent, flavouring agent, saccharine and/or carboxymethylcellulose as a thickening agent or another excipient known to those skilled in art.

A salt of the invention may also be administered in conjunction with another compound used for the treatment of one or more of the above conditions.

The invention therefore further relates to a combination therapy wherein a salt of the invention or a pharmaceutical composition or formulation comprising a salt of the invention, is administered concurrently or sequentially or as a combined preparation with another therapeutic agent or agents, for the treatment of one or more of the conditions listed.

In particular, for the treatment of an inflammatory disease such as (but not restricted to) rheumatoid arthritis, osteoarthritis, asthma, allergic rhinitis, chronic obstructive pulmonary disease (COPD), psoriasis, and inflammatory bowel disease, a salt of the invention may be combined with one of the following agents: non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a salt of the invention together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a salt of the invention with a monoclonal antibody targeting B-Lymphocytes (such as CD20 (rituximab), MRA-aIL16R and T-Lymphocytes, CTLA4-Ig, HuMax 11-15).

The present invention still further relates to the combination of a salt of the invention, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C-C family); CXCR1, CXCR2, CXCR3, CXCR4 and CXCR5 (for the C-X-C family) and $CX_3CR1$ for the C-$X_3$-C family.

The present invention further relates to the combination of a salt of the invention, with an inhibitor of matrix metalloprotease (MMPs), i.e., the stromelysins, the collagenases, and the gelatinases, as well as aggrecanase; especially collagenase-1 (MMP-1), collagenase-2(MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a salt of the invention, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746, 530; or an indole or quinoline compound such as MK-591, MK-886, and BAY x 1005.

The present invention further relates to the combination of a salt of the invention, and a receptor antagonist for leukotrienes (LT) B4, LTC4, LTD4, and LTE4. selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a salt of the invention, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a salt of the invention, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a salt of the invention, and a proton pump inhibitor (such as omeprazole) or a gastroprotective histamine type 2 receptor antagonist.

The present invention further relates to the combination of a salt of the invention, and an antagonist of the histamine type 4 receptor.

The present invention still further relates to the combination of a salt of the invention, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a salt of the invention, and an anticholinergic agents including muscarinic receptor (M1, M2, and M3) antagonist such as atropine, hyoscine, glycopyrrrolate, ipratropium bromide, tiotropium bromide, oxitropium bromide, pirenzepine or telenzepine.

The present invention further relates to the combination of a salt of the invention, and a chromone, such as sodium cromoglycate or nedocromil sodium.

The present invention still further relates to the combination of a salt of the invention, with a glucocorticoid, such as flunisolide, triamcinolone acetonide, beclomethasone dipropionate, budesonide, fluticasone propionate, ciclesonide or mometasone furoate.

The present invention further relates to the combination of a salt of the invention, with an agent that modulates a nuclear hormone receptor such as PPARs.

The present invention still further relates to the combination of a salt of the invention, together with an immunoglobulin (Ig) or Ig preparation or an antagonist or antibody modulating Ig function such as anti-IgE (for example omalizumab).

The present invention further relates to the combination of a salt of the invention, and another systemic or topically-applied anti-inflammatory agent, such as thalidomide or a derivative thereof, a retinoid, dithranol or calcipotriol.

The present invention still further relates to the combination of a salt of the invention, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a salt of the invention, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a salt of the invention, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a salt of the invention, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a salt of the invention, and an agent for the treatment of acute or chronic pain, such as a centrally or peripherally-acting analgesic (for example an opioid or derivative thereof), carbamazepine, phenyloin, sodium valproate, amitryptiline or other anti-depressant agents, paracetamol, or a non-steroidal anti-inflammatory agent.

The present invention further relates to the combination of a salt of the invention, together with a parenterally or topically-applied (including inhaled) local anaesthetic agent such as lignocaine or a derivative thereof.

A salt of the present invention can also be used in combination with an anti-osteoporosis agent including a hormonal agent such as raloxifene, or a biphosphonate such as alendronate.

The present invention still further relates to the combination of a salt of the invention together with a: (i) tryptase inhibitor; (ii) platelet activating factor (PAF) antagonist; (iii) is interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B.sub1.- or B.sub2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin $NK_1$ or $NK_3$ receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2x7; (xxvii) inhibitor of transcription factor activation such as NFkB, API, or STATS; or, (xxviii) a glucocorticoid receptor agonist.

General Preparative Methods

There follow preparative methods for N-[2-(Diethylamino)ethyl]-N-(2-{[2-(4-hydroxy-2-oxo-2,3-dihydro-1,3-benzothiazol-7-yl)ethyl]amino ethyl)-3-[2-(1-naphthyl) ethoxy]propanamide dihydrobromide (called Compound A in the Preparations, Examples and assays) and also assays and data showing the activity of this compound.

In the Examples N-[2-(Diethylamino)ethyl]-N-(2-{[2-(4-hydroxy-2-oxo-2,3-dihydro-1,3-benzothiazol-7-yl)ethyl] amino}ethyl)-3-[2-(1-naphthyl)ethoxy]propanamide is referred to as Compound B.

NMR spectra were recorded on a Varian Inova 400 MHz or a Varian Mercury-VX 300 MHz instrument. The central peaks of chloroform-d OH 7.27 ppm), dimethylsulfoxide-$d_6$ ($\delta_H$ 2.50 ppm), acetonitrile-$d_3$ ($\delta_H$ 1.95 ppm) or methanol-$d_4$ ($\delta_H$ 3.31 ppm) were used as internal references. Column chromatography was carried out using silica gel (0.040-0.063 mm, Merck). Unless stated otherwise, starting materials were commercially available. All solvents and commercial reagents were of laboratory grade and were used as received.

The following method was used for LC/MS analysis:

Instrument Agilent 1100; Column Waters Symmetry 2.1× 30 mm; Mass APCI; Flow rate 0.7 ml/min; Wavelength 254 nm; Solvent A: water+0.1% TFA; Solvent B: acetonitrile+ 0.1% TFA; Gradient 15-95%/B 8 min, 95% B 1 min.

Analytical chromatography was run on a Symmetry $C_{18}$-column, 2.1×30 mm with 3.5 μm particle size, with acetonitrile/water/0.1% trifluoroacetic acid as mobile phase in a gradient from 5% to 95% acetonitrile over 8 minutes at a flow of 0.7 ml/min.

Instrument Details:

XRPD (X-ray powder diffraction)—Philips X-Pert MPD machine in θ-θ configuration over the scan range 2° to 40° 2θ with 100-second exposure per 0.03° increment. The X-rays were generated by a copper long-fine focus tube operated at 45 kV and 40 mA. The wavelengths of the copper X-rays were 1.5405 Å ($K_{\alpha 1}$) and 1.5444 Å ($K_{\alpha 2}$). The Data was collected on zero background holders on which ~2 mg of the compound was placed. The holder was made from a single crystal of silicon, which had been cut along a non-diffracting plane and then polished on an optically flat finish. The X-rays incident upon this surface were negated by Bragg extinction. XRPD data are presented in the tables below, and reflection angle (° 2θ) and D-spacing (Å) data (bracketed) are provided.

DSC (Differential Scanning Calorimetry) thermograms were measured using a TA Q1000 machine, with aluminium pans and pierced lids. The sample weights varied between 1 to 5 mg. The procedure was carried out under a flow of nitrogen gas (50 ml/min) and the temperature studied from 25 to 300° C. at a constant rate of temperature increase of 10° C. per minute.

TGA (Thermogravimetric Analysis) thermograms were measured using a TA Q500 machine, with platinum pans. The sample weights varied between 2 and 15 mg. The procedure was carried out under a flow of nitrogen gas (60 ml/min) and the temperature studied from 25 to 300° C. at a constant rate of temperature increase of 10° C. per minute.

$^{13}$C CPMAS (Cross Polarisation Magic Angle Spinning) Solid State NMR spectra were obtained using a Bruker Avance 400WB machine. Samples were analysed using a 4 mm probe and under the following parameters: ramped cross polarisation, tppm 15 composite pulse, $^1$H decoupling, a contact time of 2 ms, and a spin rate of 5 kHz.

Raman spectra were recorded using a Jobin Yvon Horiba Lab Ram HR raman microscope. The solid sample ~0.1 mg, was placed onto a glass slide and the laser beam was focused onto a single particle that was representative of the bulk sample. Spectra were recorded as 2-4 minute acquisition over the range of 200 to 2000 $cm^{-1}$.

IR spectra were recorded using a Perkin Elmer Spectrum GX FT-IR System machine equipped with a Specac ATR attachment. The solid sample ~1 mg, was placed onto the diamond surface of the ATR and a pressure of 70cN-M was applied. Spectra were recorded as 64 scans over the range of 4000 to 625 $cm^{-1}$, with an interval of 1 $cm^{-1}$ and a resolution of 4 $cm^{-1}$.

GVS profiles were measured using a Dynamic Vapour Sorption DVS-1 instrument. The solid sample ca. 4-10 mg was placed into a glass vessel and the weight of the sample was recorded during a dual cycle step method (40 to 90 to 0 to 90 to 0% relative humidity (RH), in steps of 10% RH).

Ion-Stoichiometry—was measured using a KOH gradient and a Dionex AS11 column with electrochemical detection and a Dionex IC3000 instrument.

Solution $^1$H NMR spectra were recorded using a Varian Unity Inova spectrometer at a proton frequency of 400 MHz.

The abbreviations or terms used in the examples have the following meanings:

SCX: Solid phase extraction with a sulfonic acid sorbent
HPLC: High performance liquid chromatography
DMF: N,N-Dimethylformamide Preparation 1

N-[2-(Diethylamino)ethyl]-N-(2-{[2-(4-hydroxy-2-oxo-2,3-dihydro-1,3-benzothiazol-7-yl)ethyl] amino}ethyl)-3-[2-(1-naphthyl)ethoxy]propanamide dihydrobromide (Compound A)

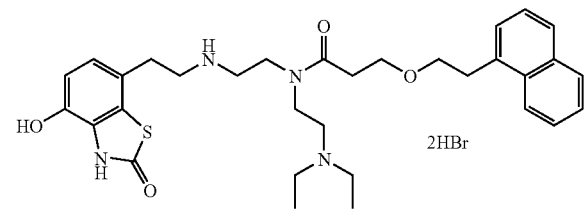

a) tert-Butyl 3-[2-(1-naphthyl)ethoxy]propanoate

1-Naphthalene ethanol (10 g) was treated with benzyltrimethylammonium hydroxide (Triton B®; 0.9 mL of a 40% solution in methanol) and the resulting mixture stirred in vacuo for 30 minutes. The mixture was then cooled to 0° C. and treated with tert-butyl acrylate (8.19 g). The resulting mixture was slowly warmed to room temperature and stirred overnight. The crude mixture was subsequently absorbed onto aluminium oxide (30 g) and eluted with diethylether (200 mL). The organics were concentrated to give a crude material (16.6 g) which was purified by flash silica chromatography eluting with 1:8, diethylether:hexane to give the subtitled compound (12.83 g).

$^1$H NMR (CDCl$_3$) δ 8.05 (dd, 1H), 7.84 (dd, 1H), 7.72 (dd, 1H), 7.54-7.34 (m, 4H), 3.81-3.69 (m, 4H), 3.35 (t, 2H), 2.52-2.47 (m, 2H), 1.45 (s, 9H).

b) 3-[2-(1-Naphthyl)ethoxy]propanoic acid tert-Butyl 3-[2-(1-naphthyl)ethoxy]propanoate (6.19 g) was taken up in dichloromethane (30 mL) and treated with trifluoroacetic acid (5 mL). The resulting solution was stirred at room temperature for 2 hours, an additional 1 mL of trifluoroacetic acid was added and the solution stirred overnight. The mixture was concentrated, taken up in 2M sodium hydroxide solution (30 mL) and washed with ether (2×20 mL). The aqueous layer was subsequently acidified (using 1M hydrochloric acid) and extracted with ether (2×30 mL). The combined organics were washed with brine (20 mL), dried over anhydrous magnesium sulphate, filtered and concentrated in vacuo to give the sub-titled compound (5.66 g) as a clear oil.

$^1$H NMR (CDCl$_3$) δ 8.05 (bs, 1H), 7.85 (bs, 1H), 7.74 (bs, 1H), 7.50-7.38 (m, 4H), 3.84-3.75 (bm, 4H), 3.39 (bs, 2H), 2.65 (bs, 2H).

c) N-(2-Diethylaminoethyl)-N-(2-hydroxyethyl)-3-[2-(1-naphthyl)ethoxy]-propanamide Oxalyl chloride (0.33 g) was added dropwise to a solution of 3-[2-(1-naphthyl)ethoxy]propanoic acid (0.53 g) in dichloromethane (10 mL), dimethylformamide (1 drop) was added and stirring continued at room temperature for 1 hour. The mixture was subsequently concentrated, re-dissolved in dichloromethane (10 mL) and added dropwise to a solution of 2-(2-diethylaminoethylamino)ethanol (0.35 g) and diisopropylethylamine (0.56 g) in dichloromethane (10 mL). The resulting mixture was stirred at room temperature for 1 hour, diluted (dichloromethane, 50 mL), washed with water (2×20 mL), brine (20 mL), dried over magnesium sulfate and concentrated to give the crude product (0.91 g) which was purified by flash column chromatography (eluting with 5-7% methanol in dichloromethane) to give 0.63 g of the sub-titled compound.

$^1$H NMR (CDCl$_3$) δ 8.05 (d, 1H), 7.85 (d, 1H), 7.73 (d, 1H), 7.52-7.47 (m, 2H), 7.42-7.35 (m, 2H), 3.84-3.78 (m, 6H), 3.72-3.70 (m, ½H), 3.45-3.35 (m, 6H), 2.79-2.77 (m, 1+½H), 2.62-2.58 (m, 2H), 2.54-2.49 (m, 4H), 1.04-1.01 (m, 6H).

d) N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide A solution of dimethylsulfoxide (0.097 g) in dichloromethane (1 mL) was added to a solution of oxalyl chloride (0.079 g) in dichloromethane (10 mL) at −78° C. The reaction was stirred for 15 minutes and then a solution of N-(2-diethylaminoethyl)-N-(2-hydroxyethyl)-3-[2-(1-naphthyl)ethoxy] propanamide (0.22 g) in dichloromethane (1 mL+1 mL wash) was added and the reaction mixture stirred for a further 15 minutes. Triethylamine (0.29 g) was added and the reaction allowed to warm to room temperature over 1 hour, the mixture was subsequently diluted (dichloromethane 30 mL), the organics washed with sodium bicarbonate (20 mL), brine (20 mL), dried over anhydrous magnesium sulphate, filtered and concentrated in vacuo to give the sub-titled compound (0.21 g).

The crude product was dissolved in methanol (10 mL) and 7-(2-aminoethyl)-4-hydroxy-1,3-benthiazol-2(3H)-one hydrochloride (prepared according to the procedure outlined in Organic Process Research & Development 2004, 8(4), 628-642; 0.131 g) was added along with acetic acid (0.1 mL) and water (0.1 mL). After stirring at room temperature for 30 minutes, sodium cyanoborohydride (0.020 g) was added and the reaction mixture was stirred overnight. Ammonia (7N in methanol, 1 mL) was added and the mixture was concentrated. The crude residue was purified by flash column chromatography eluting with 1% ammonia; 5%-7% methanol in dichloromethane. The crude product was used directly in the next step.

A repreparation of N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide provided a sample that was analysed.

$^1$H NMR (400 MHz, DMSO) δ 8.06 (d, 1H), 7.90 (d, 1H), 7.77 (d, 1H), 7.51 (m, 2H), 7.40 (m, 2H), 6.80 (m, 1H), 6.70 (m, 1H), 3.68 (m, 4H), 3.27 (m, 6H), 2.79-2.53 (number of protons could not be determined), 2.44 (m, 4H), 0.92 (m, 6H).

See FIG. 1, which shows the XRPD of Amorphous form of Compound B e) N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide dihydrobromide

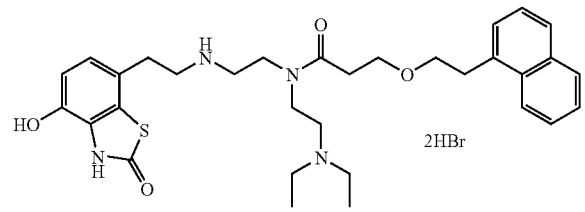

N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide (0.052 g) was dissolved in ethanol (1.5 mL) and treated with 48% hydrobromic acid (21 µl). The white solid dihydrobromide salt (0.058 g) was collected by filtration.

MS: APCI(+ve) 579 (M+1)

$^1$H NMR δ(DMSO) 11.78-11.71 (m, 1H), 10.11-10.06 (m, 1H), 9.51-9.43 (m, 0.33H), 9.21-9.13 (m, 0.66H), 8.75-8.66 (m, 1H), 8.59-8.51 (m, 1H), 8.06 (d, 1H), 7.95-7.90 (m, 1H), 7.79 (d, 1H), 7.60-7.48 (m, 2H), 7.47-7.39 (m, 2H), 6.87 (t, 1H), 6.76 (dd, 1H), 3.78-3.53 (m, 10H), 3.25-3.09 (m, 10H), 2.91-2.80 (m, 2H), 2.73-2.61 (m, 2H), 1.26-1.15 (m, 61-1). NMR indicates approximately 2:1 mixture of rotamers at 298K.

| XRPD (FIG. 2) 2θ(d spacing) | | DSC | Solid State NMR | | Raman | | IR | |
|---|---|---|---|---|---|---|---|---|
| 4.9(17.9) | 26.2(3.4) | Onset 211° C. | 232.4 | 63.7 | 204.1 | 1240.8 | 205 | 1276 |
| 8.9(9.9) | 28.0(3.2) | | 225.8 | 48.4 | 233.5 | 1276.8 | 236 | 1379 |
| 12.2(7.3) | 28.4(3.1) | | 224.5 | 44.9 | 246.5 | 1374.7 | 300 | 1436 |
| 13.5(6.6) | 31.0(2.9) | | 190.9 | 39.8 | 367.5 | 1434.7 | 368 | 1465 |
| 13.9(6.4) | 31.6(2.8) | | 182.7 | 36.2 | 394.6 | 1452.0 | 395 | 1577 |
| 14.8(6.0) | 33.0(2.7) | | 180.6 | 33.5 | 440.1 | 1577.1 | 441 | 1586 |
| 15.8(5.6) | | | 164.0 | 27.9 | 470.0 | 1595.9 | 471 | 1597 |
| 16.2(5.5) | | | 141.2 | 9.2 | 488.9 | 1633.7 | 490 | 1633 |
| 16.6(5.4) | | | 134.8 | 6.0 | 505.3 | 1689.1 | 506 | 1689 |
| 17.4(5.1) | | | 132.9 | | 590.3 | | 591 | |
| 18.1(4.9) | | | 130.8 | | 642.5 | | 643 | |
| 19.3(4.6) | | | 127.5 | | 725.4 | | 726 | |
| 20.3(4.4) | | | 123.1 | | 789.5 | | 790 | |
| 20.7(4.3) | | | 120.9 | | 807.7 | | 807 | |
| 21.4(4.2) | | | 114.2 | | 855.0 | | 855 | |
| 22.9(3.9) | | | 91.4 | | 924.0 | | 942 | |
| 23.7(3.8) | | | 85.0 | | 1028.7 | | 1029 | |
| 24.3(3.7) | | | 75.3 | | 1075.1 | | 1069 | |
| 25.6(3.5) | | | 66.6 | | 1143.9 | | 1241 | |

See FIG. 2, which shows the XRPD of Polymorph A of Compound A.

Preparation 2

N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide dihydrobromide (Compound A)

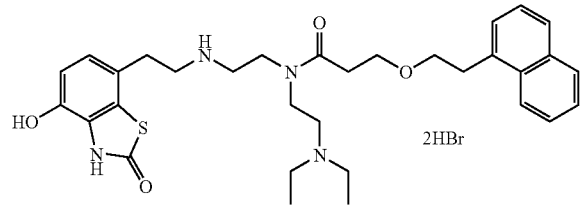

a) N'-(2,2-Dimethoxyethyl)-N,N-diethyl-ethane-1,2-diamine

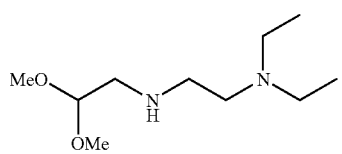

A solution of N,N-diethyl-ethylenediamine (150 g) in methanol (500 mL) was treated dropwise rapidly with glyoxal dimethylacetal (60 wt % soln. in water, 225 g) at 10-15° C. After the addition was complete the solution was warmed to 15° C., then to 22° C. and left at this temperature for 16 hours. The reaction mixture was treated with 5% palladium on carbon (Johnson-Matthey type 38H paste, 15 g) and hydrogenated at 6 bar until the reaction was complete as judged by GC/MS. The catalyst was removed by filtration and the filtrate evaporated to dryness (toluene azeotrope, 2.5 L), affording 196.2 g of the sub-titled compound.

$^1$H NMR (CDCl$_3$): 4.48 (t, 1H), 3.39 (s, 6H), 2.75 (d, 2H), 2.69 (t, 2H), 2.57-2.48 (m, 6H), 1.01 (ts, 6H).

b) N-[2-(Diethylamino)ethyl]-N-(2,2-dimethoxyethyl)-3-[2-(1-naphthyl)ethoxy]propanamide

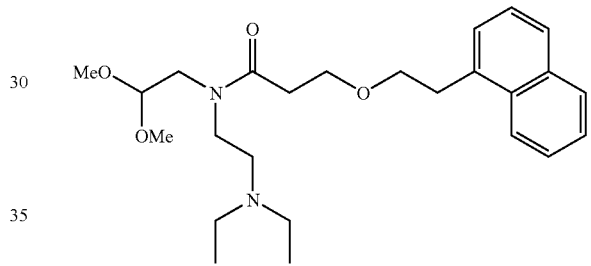

Oxalyl chloride (151 mL) was added dropwise over 45 minutes to a solution of 3-[2-(1-naphthyl)ethoxy]propanoic acid (389 g) (Example 7 step b)) in dichloromethane (2.1 L) and DMF (0.5 mL). The reaction mixture was stirred for a further 16 hours. The mixture was subsequently concentrated, redissolved in DCM (1.7 L) and added dropwise over 1.75 hours at 0° C. to a solution of N'-(2,2-dimethoxyethyl)-N,N-diethylethane-1,2-diamine (325 g) and isopropyldiethylamine (551 mL) in DCM (1.7 L). The resulting mixture was stirred at room temperature for 3 hours, washed with aqueous saturated sodium bicarbonate solution (5×1 L), water (1.5 L) and dried over sodium sulphate and concentrated to give 650 g of the sub-titled compound.

m/e 431 (M+H$^+$, 100%)

c) N-[2-(Diethylamino)ethyl]-3-[2-(1-naphthyl)ethoxy]-N-(2-oxoethyl)propanamide

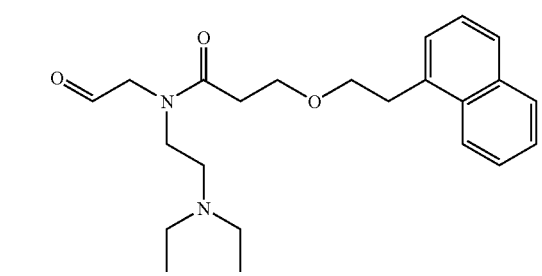

A solution of N-[2-(diethylamino)ethyl]-N-(2,2-dimethoxyethyl)-3-[2-(1-naphthyl)ethoxy]propanamide (93 g) in DCM (270 mL) was treated dropwise at 0° C. with trifluoroacetic acid (270 mL) over 1.5 hours. After the addition the reaction mixture was allowed to warm to room temperature and stirred for a further 1 hour. The reaction mixture was concentrated and the residue poured into aqueous saturated sodium bicarbonate solution (1800 mL, caution). The aqueous mixture was extracted with DCM (4×400 mL) and the combined extracts were dried over magnesium sulphate and concentrated. The residue was used directly in the following reaction.

d) N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide dihydrobromide (Compound A)

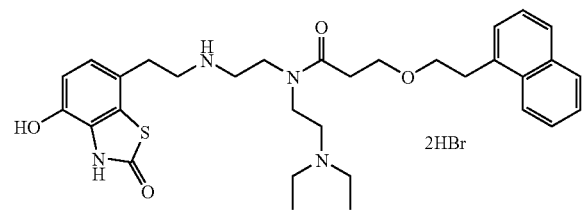

A suspension of 7-(2-amino-ethyl)-4-hydroxy-3H-benzothiazol-2-one hydrochloride (53 g) in dry NMP (216 mL) was heated to 60° C. and treated in one portion with a solution of NaOH (8.2 g) in methanol (102 mL). The bright orange suspension was cooled to room temperature and treated dropwise with a solution of N-[2-(diethylamino)ethyl]-3-[2-(1-naphthyl)ethoxy]-N-(2-oxoethyl)propanamide in dichloromethane (475 mL) over 20 minutes. The reaction was left to stir for 25 minutes. Sodium triacetoxyborohydride (91.5 g) was then added in portions over 20 minutes and the mixture stirred for a further 50 minutes. The reaction mixture was poured into water (1.8 L) and the acidic solution (pH5) was washed with tert. butyl methyl ether (TBME) (3×500 mL). The aqueous phase was basified to pH8 by the addition of solid potassium carbonate and extracted with dichloromethane (3×750 mL); the combined organic extracts were dried over magnesium sulphate and concentrated to give a dark oil. This was dissolved in ethanol (200 mL) and 48% aqueous hydrobromic acid (73 mL) was added. The solution was aged for 30 minutes then evaporated to dryness. The residue was triturated with ethanol (560 mL); the resultant solid was collected by filtration and dried in vacuo at 50° C. The sticky solid was suspended in boiling ethanol (100 mL) and filtered while hot. The collected solid was dried in vacuo at 50° C. This material was recrystallised from ethanol/water (3:1, 500 mL). After standing overnight the resultant solid was collected by filtration and washed with ice-cold ethanol (75 mL). Drying in vacuo at 50° C. for 24 hr afforded 57 g of the title compound.

Preparation 3

N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide (Compound B)

N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide dihydrobromide (10 g) was partitioned between saturated sodium bicarbonate solution (100 mL) and dichloromethane (100 mL) (a little methanol was added to aid solubility). The mixture was stirred at RT for 1 hr.

The phases were then separated and the aqueous phase was extracted with a further portion of dichloromethane (100 mL). The combined organic phase was washed with saturated sodium bicarbonate solution (100 mL) and saturated brine solution (100 ml) then dried over magnesium sulfate, filtered and evaporated to leave the title compound (8.66 g).
$^1$H NMR (400 MHz, DMSO) δ 8.06 (d, 1H), 7.90 (d, 1H), 7.77 (d, 1H), 7.51 (m, 2H), 7.40 (m, 2H), 6.80 (m, 1H), 6.70 (m, 1H), 3.68 (m, 4H), 3.27 (m, 6H), 2.79-2.53 (number of protons could not be determined), 2.44 (m, 4H), 0.92 (m, 6H).

Preparation 4

N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide dihydrobromide (Compound A)

A suspension of N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide dihydrobromide (prepared, for example, as in Preparation 2) (1.88 kg) in 80:20 isopropanol:water (20.97 kg) was heated to reflux. The solution was then filtered and the filtrate was allowed to cool to 50° C. before a seed of N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide dihydrobromide (1.08 g) was added. The temperature was held at 50° C. for 20 mins then the reaction mixture was cooled to 5° C. at a rate of 0.1° C./min. The suspension was held at 5° C. for 3 days then the precipitated material was collected by filtration. The cake was washed with 80:20 isopropanol:water (2.91 kg). The solid was then dried in vacuo at 40° C. to constant weight to give the title compound (1.545 kg). $^1$H NMR (400 MHz, DMSO, 90° C.) δ 11.50-8.52 (m, 3H), 8.06 (d, 1H), 7.90 (d, 1H), 7.77 (d, 1H), 7.52 (m, 2H), 7.42 (m, 2H), 6.87 (d, 1H), 6.76 (d, 1H), 3.74 (m, 4H), 3.61 (br, 4H), 3.29 (t, 2H), 3.2-3.0 (number of protons could not be determined), 2.87 (m, 2H), 2.65 (t, 2H), 1.22 (t, 6H).

Preparation 5

N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide dihydrochloride A 37 wt/wt % solution of hydrochloric acid (245.95 µL) was added to a solution of N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide (0.56 g) in methanol (5.6 mL) producing a clear solution that was stirred at room temperature for 15 mins. A 0.5 mL aliquot was taken from the bulk of the solution and treated with diethyl ether to form a mobile solid. This suspension was added back to the solution and the mixture was stirred at room temperature for 2 h. The title compound was then collected by filtration, washed with methanol (1.12 mL) and dried on the filter (0.46 g).
$^1$H NMR (400 MHz, DMSO, 90° C.) δ 11.46 (m, 1H), 8.06 (d, 1H), 7.88 (d, 1H), 7.75 (d, 1H), 7.55-7.38 (m, 4H), 6.88 (d, 1H), 6.76 (d, 1H), 3.74 (m, 8H), 3.28 (t, 2H), 3.2-3.0 (number of protons could not be determined), 2.92 (m, 2H), 2.66 (t, 2H), 1.25 (t, 6H).

Calc for $C_{32}H_{44}Cl_2N_4O_4S$: C, 58.98; H, 6.81; N, 8.60; S, 4.92. Found: C, 58.89; H, 6.87; N, 8.58; S, 5.24.

| XRPD (FIG. 3) | DSC | | Solid State NMR | | Raman | | IR | |
|---|---|---|---|---|---|---|---|---|
| 4.9(18.2) | 27.9(3.20) | Onset-192° C. | 232.4 | 66.6 | 207.8 | 1379.3 | 3163 | 946 |
| 7.7(11.5) | 28.2(3.16) | | 225.8 | 63.7 | 242.2 | 1412.2 | 2981 | 927 |
| 8.9(10.0) | 28.5(3.13) | | 224.5 | 51.9 | 310.8 | 1437.1 | 2877 | 868 |
| 9.2(9.6) | 29.1(3.07) | | 190.9 | 48.4 | 368.2 | 1451.2 | 2787 | 844 |
| 12.0(7.4) | 30.6(2.92) | | 184.5 | 36.2 | 395.6 | 1483.5 | 2428 | 812 |
| 12.5(7.1) | 32.1(2.78) | | 182.7 | 31.7 | 470.6 | 1576.9 | 1683 | 797 |
| 13.7(6.5) | | | 180.6 | 27.9 | 490.5 | 1599.3 | 1631 | 741 |
| 14.8(6.0) | | | 164.0 | 8.6 | 505.6 | 1634.7 | 1514 | 721 |
| 15.9(5.6) | | | 141.2 | 5.8 | 594.4 | 1687.3 | 1467 | 644 |
| 16.4(5.4) | | | 134.8 | | 642.8 | | 1435 | |
| 16.9(5.2) | | | 132.9 | | 694.4 | | 1420 | |
| 18.5(4.81) | | | 130.8 | | 726.0 | | 1393 | |
| 19.4(4.58) | | | 123.1 | | 807.7 | | 1335 | |
| 21.1(4.21) | | | 114.2 | | 854.4 | | 1293 | |
| 23.17(3.84) | | | 91.4 | | 926.3 | | 1183 | |
| 24.8(3.60) | | | 85.0 | | 1029.8 | | 1144 | |
| 25.4(3.50) | | | 83.2 | | 1073.9 | | 1113 | |
| 26.0(3.43) | | | 81.1 | | 1185.8 | | 1059 | |
| 27.1(3.29) | | | 77.7 | | 1276.8 | | 1019 | |

See FIG. 3, which shows the XRPD of Polymorph A of dihydrochloride salt of Compound B.

The following Examples illustrate the invention.

Example 1

N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide citrate Citric Acid (248.96 mg) was added to a solution of N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide (0.5 g) in methanol (5 mL). Immediately, the clear solution became opaque and orange oil settled out. This mixture was heated at an external temp of 60° C. forming a clear solution, which was then allowed to cool to room temperature and stirred for 48 h. The resulting precipitate was collected by filtration and washed with methanol (1 mL) and diethyl ether (1 mL). The solid was then dried in vacuo at room temperature for 4 h to give the title compound (0.3 g).

$^1$H NMR (400 MHz, DMSO, 90° C.) δ 8.06 (d, 1H), 7.88 (d, 1H), 7.75 (d, 1H), 7.50 (m, 2H), 7.39 (m, 2H), 6.82 (d, 1H), 6.72 (d, 1H), 3.75 (t, 2H), 3.70 (t, 2H), 3.6-3.3 (number of protons could not be determined), 3.28 (t, 2H), 3.1-2.4 (number of protons could not be determined), 0.99 (br, 6H).

See FIG. 4 which shows the XRPD of Di-Hydrate Polymorph A of Citrate Salt of Compound B.

| XRPD (FIG. 4) | DSC | | Solid State NMR | | Raman | | IR | |
|---|---|---|---|---|---|---|---|---|
| 4.4(20.3) | 21.4(4.14) | Onset 112° C. | 228.2 | 48.1 | 269.7 | 1141.6 | 2979 | 868 |
| 6.2(14.3) | 24.2(3.69) | | 226.2 | 45.0 | 295.1 | 1281.4 | 2864 | 838 |
| 7.2(12.2) | 25.8(3.46) | | 184.1 | 43.5 | 373.7 | 1371.2 | 2616 | 799 |
| 7.8(11.3) | 27.2(3.28) | | 181.9 | 37.3 | 406.2 | 1440.8 | 2459 | 748 |
| 8.6(10.3) | 27.9(3.19) | | 178.5 | 32.9 | 434.4 | 1482.9 | 1686 | 695 |
| 11.0(8.1) | 31.7(2.82) | | 176.4 | 25.9 | 470.6 | 1515.0 | 1626 | 663 |
| 12.3(7.2) | | | 171.9 | 8.7 | 511.8 | 1578.9 | 1561 | |
| 12.9(6.9) | | | 170.5 | 6.5 | 553.3 | 1624.6 | 1514 | |
| 13.7(6.5) | | | 141.8 | 2.8 | 597.5 | 1702.0 | 1455 | |
| 14.4(6.1) | | | 134.3 | | 667.5 | | 1416 | |
| 14.8(6.0) | | | 128.7 | | 699.3 | | 1371 | |
| 15.6(5.7) | | | 126.8 | | 715.4 | | 1324 | |
| 16.0(5.5) | | | 125.6 | | 802.3 | | 1280 | |
| 16.9(5.2) | | | 124.0 | | 846.9 | | 1231 | |
| 17.4(5.1) | | | 122.5 | | 865.1 | | 1182 | |
| 18.7(4.75) | | | 120.4 | | 938.9 | | 1108 | |
| 19.2(4.63) | | | 109.1 | | 981.7 | | 1058 | |
| 20.6(4.32) | | | 77.0 | | 1026.4 | | 934 | |
| 21.0(4.22) | | | 70.8 | | 1078.5 | | 900 | |

Example 2

N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide ditosylate p-Toluenesulfonic acid monohydrate (667.33 mg) was added in one portion to a solution of N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide (1 g) in methanol (10 mL) producing a clear solution. This was stirred at room temperature for 30 mins then the solvent was removed in vacuo. The residue was stirred in diethyl ether (20 mL) at room temperature for 16 h then the solvent was removed and methyl t-butyl ether (20 mL) was added. This mixture was then stirred at room temperature for 16 h before the resulting solid was collected by filtration and washed with methyl t-butyl ether (5 mL). The title compound was dried in vacuo at room temperature for 16 h to leave the title compound as an amorphous solid (1.18 g).

$^1$H NMR (400 MHz, DMSO, 90° C.) δ 11.35 (1H, br), 8.05 (d, 1H), 7.88 (d, 1H), 7.76 (d, 1H), 7.51 (m, 6H), 7.40 (m, 2H), 7.09 (d, 4H), 6.83 (d, 1H), 6.74 (d, 1H), 3.77 (t, 2H), 3.72 (t, 2H), 3.64 (br, 4H), 3.4-3.0 (number of protons could not be determined), 2.85 (m, 2H), 2.64 (t, 2H), 2.28 (s, 6H), 1.22 (t, 6H).

See FIG. 5, which shows the XRPD of Amorphous form of Di-Tosylate Salt of Compound B.

Example 3

N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide phosphate Di-Hemi-Hydrate Phosphoric Acid (199.19 mg) was added to a solution of N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide (1 g) in methanol (10 mL) producing a gum. The mixture was heated to reflux, and on continued stirring gave a mobile solid. The suspension was allowed to cool slowly to room temperature then filtered and the cake was washed with methanol (2 mL). The title compound (0.93 g) was allowed to dry on the filter.

$^1$H NMR (400 MHz, DMSO, 90° C.) δ 8.05 (d, 1H), 7.87 (d, 1H), 7.74 (m, 1H), 7.48 (m, 2H), 7.38 (m, 2H), 6.78 (d, 1H), 6.68 (d, 1H), 3.73 (t, 2H), 3.67 (t, 2H), 3.31 (m, number of protons could not be determined), 3.26 (t, 2H), 2.8-2.3 (number of protons could not be determined), 0.94 (t, 6H).

See FIG. 6, which shows the XRPD of Di-Hemi-Hydrate Polymorph A of Phosphate Salt of Compound B

| XRPD (FIG. 6) | | DSC | Solid State NMR | | Raman | IR |
|---|---|---|---|---|---|---|
| 5.5(16.1) | 22.8(3.90) | Onset 94° C. | 223.1 | 80.3 | 372.7 | 1199.5 | 2987 |
| 8.4(10.5) | 23.4(3.79) | | 193.1 | 72.5 | 403.0 | 1278.7 | 2877 |
| 9.04(9.8) | 24.3(3.65) | | 183.6 | 65.4 | 736.0 | 1300.5 | 2392 |
| 9.7(9.1) | 25.1(3.54) | | 182.0 | 49.3 | 472.2 | 1372.3 | 1686 |
| 10.5(8.4) | 26.0(3.43) | | 176.8 | 45.8 | 513.1 | 1440.3 | 1630 |
| 11.8(7.5) | 27.0(3.30) | | 173.2 | 33.7 | 536.5 | 1517.3 | 1513 |
| 12.9(6.9) | 28.5(3.13) | | 170.4 | 28.5 | 565.2 | 1580.2 | 1443 |
| 13.6(6.5) | | | 167.7 | 9.4 | 598.7 | 1622.8 | 1397 |
| 15.0(5.9) | | | 161.7 | 9.1 | 668.4 | 1699.9 | 1291 |
| 15.8(5.6) | | | 143.3 | | 696.5 | | 1200 |
| 16.3(5.4) | | | 133.9 | | 711.8 | | 1141 |
| 16.8(5.3) | | | 127.0 | | 779.6 | | 1100 |
| 17.8(5.0) | | | 124.5 | | 854.4 | | 1019 |
| 18.3(4.85) | | | 121.6 | | 941.3 | | 868 |
| 19.3(4.60) | | | 119.3 | | 989.0 | | 842 |
| 19.3(4.59) | | | 117.9 | | 1022.4 | | 791 |
| 19.8(4.47) | | | 112.0 | | 1062.0 | | 695 |
| 20.6(4.30) | | | 84.1 | | 1104.4 | | 670 |
| 21.9(4.06) | | | 82.6 | | 1143.9 | | |

Example 4A

N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide dixinafoate di-hydrate A suspension of 1-hydroxy-2-naphthoic acid (328.42 mg) in methanol (3 mL) was added to a solution of N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propan-amide (0.5 g) in methanol (3 mL) and the resulting mixture was heated to reflux then allowed to cool to room temperature and stirred for 16 h. The title compound was filtered, washed with methanol (1 mL) and dried in vacuo at room temperature for 1 h (0.47 g).

$^1$H NMR (400 MHz, DMSO, 90° C.) δ 8.24 (d, 2H), 8.04 (d, 1H), 7.87 (d, 1H), 7.75 (m, 5H), 7.50 (m, 4H), 7.40 (m, 4H), 7.11 (d, 2H), 6.83 (d, 1H), 6.73 (d, 1H), 3.75 (t, 2H), 3.70 (t, 2H), 3.6-3.3 (m, 4H), 3.26 (t, 2H), 2.6-3.1 (number of protons could not be determined), 2.59 (t, 2H), 1.05 (br, 6H).

| XRPD (FIG. 7) | DSC | Solid State NMR | | Raman | IR | |
|---|---|---|---|---|---|---|
| 4.8(18.4) | 24.9(3.58) | Onset 92° C. | 226.9 | 50.1 | 232.8 | 1159.1 | 3162 | 741 |
| 7.7(11.5) | 26.0(3.43) | | 210.0 | 49.0 | 287.2 | 1201.4 | 2983 | 723 |
| 9.1(9.8) | 26.4(3.38) | | 187.3 | 43.2 | 326.9 | 1256.5 | 2878 | 696 |
| 9.5(9.3) | 27.5(3.24) | | 185.7 | 33.1 | 360.7 | 1371.5 | 2429 | 651 |
| 10.8(8.2) | 30.3(2.95) | | 164.8 | 29.3 | 405.6 | 1398.8 | 1683 | |
| 12.2(7.3) | | | 161.9 | 26.2 | 424.8 | 1432.0 | 1631 | |
| 12.8(6.9) | | | 160.2 | 25.7 | 475.6 | 1467.1 | 1513 | |
| 15.4(5.7) | | | 159.6 | 7.8 | 492.0 | 1579.4 | 1435 | |
| 16.1(5.5) | | | 142.4 | 3.7 | 514.7 | 1626.4 | 1420 | |
| 17.2(5.2) | | | 137.5 | | 532.4 | | 1400 | |
| 18.6(4.76) | | | 136.0 | | 556.4 | | 1293 | |
| 19.1(4.64) | | | 133.9 | | 591.2 | | 1203 | |
| 19.9(4.46) | | | 131.5 | | 623.6 | | 1184 | |
| 20.5(4.33) | | | 126.8 | | 656.7 | | 1142 | |
| 21.3(4.17) | | | 125.0 | | 693.5 | | 1113 | |
| 22.8(3.90) | | | 75.3 | | 726.0 | | 1020 | |
| 23.3(3.82) | | | 71.5 | | 787.1 | | 868 | |
| 23.6(3.77) | | | 68.0 | | 1020.6 | | 843 | |
| 24.3(3.66) | | | 51.2 | | 1095.3 | | 799 | |

See FIG. 7, which shows XRPD of Di-Hydrate Polymorph A of Di-Xinafoate Salt of Compound B.

Example 4B

N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide dixinafoate Di-Hemi-Hydrate 20 mg of Di-Hydrate Polymorph A (Example 4A) was slurried in water (0.5 ml) for one week. The resulting suspension was centrifuged and the supernatant was separated from the solid material, the latter being left to air dry overnight in a fume hood.

| XRPD (FIG. 8) | DSC | |
|---|---|---|
| 4.8(18.58) | 21.4(4.15) | Onset below 90° C. |
| 7.5(11.9) | 22.4(3.98) | |
| 7.8(11.4) | 24.7(3.60) | |
| 8.5(10.4) | 25.2(3.53) | |
| 8.8(10.0) | 25.6(3.48) | |
| 9.4(9.4) | 26.1(3.41) | |
| 10.6(8.3) | | |
| 11.6(7.7) | | |
| 11.9(7.5) | | |
| 12.3(7.2) | | |
| 12.7(7.0) | | |
| 13.4(6.6) | | |
| 15.3(5.8) | | |
| 15.6(5.7) | | |
| 16.6(5.33) | | |
| 17.7(5.0) | | |
| 18.4(4.83) | | |
| 18.7(4.76) | | |
| 18.8(4.71) | | |

See FIG. 8, which shows the XRPD of Di-Hemi-Hydrate Polymorph A of Di-Xinafoate Salt of Compound B.

Example 5

N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide sulfate Concentrated sulphuric acid (23.98 μL) was added dropwise to a solution of N-[2-(diethylamino)ethyl]-N-(2-[2-(4-hydroxy-2-oxo-2,3-dihydro-1,3-benzothiazol-7-yl)ethyl]amino}ethyl)-3-[2-(1-naphthyl)ethoxy]propanamide (0.25 g) in methanol (2.5 mL). The mixture was stirred at room temperature for 20 mins then heated at an external temperature of 60° C. then allowed to cool back to room temperature. Methyl t-butyl ether (0.5 mL) was then added and the mixture was heated at an external temperature of 60° C. then allowed to room temperature. The mixture was transferred to another flask using methanol to dissolve the mixture and then the solvent was removed in vacuo. Methyl t-butyl ether (10 mL) was added to the residue and the mixture was stirred at room temperature for 16 h. The title compound was collected by filtration and dried on the filter (0.24 g). Solid found to be amorphous.

$^1$H NMR (400 MHz, DMSO, 90° C.) δ 8.05 (m, 1H), 7.88 (m, 1H), 7.75 (m, 1H), 7.50 (m, 2H), 7.38 (m, 2H), 6.85 (m, 1H), 6.73 (m, 1H), 3.74 (m, 4H), 3.58-3.40 (m, number of protons could not be determined), 3.28 (t, 2H), 3.03-2.73 (m, number of protons could not be determined), 2.60 (t, 2H), 1.09 (s, 6H).

See FIG. 9, which shows the XRPD of Amorphous form of Sulphate Salt of Compound B.

Example 6

N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide mono benzoate Benzoic acid (52.75 mg) was added in one portion to a solution of N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide (0.25 g) in methanol (2.5 mL) producing a clear solution. This was stirred at room temperature for 1 h then the solvent was removed in vacuo. The residue was stirred in acetonitrile (5 mL) at room temperature for 16 h then the solvent was removed and methyl t-butyl ether (10 mL) was added. This mixture was stirred at room temperature for 3 h before the title compound was collected by filtration. The title compound was isolated as an amorphous solid.

$^1$H NMR (400 MHz, DMSO, 90° C.) δ 8.04 (m, 1H), 7.94 (m, 2H), 7.87 (m, 1H), 7.73 (m, 1H), 7.57-7.34 (m, 7H), 6.84-6.68 (m, 2H), 3.80-3.54 (m, 6H), 3.30 (m, could not be established due to overlap with water), 2.78-2.37 (m, number of protons could not be determined), 0.91 (m, 6H).

See FIG. 10, which shows the XRPD of Amorphous form of Mono Benzoate of Compound B.

Example 6A

N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide mono benzoate as a crystalline form 20 mg of the amorphous form of the mono-benzoate salt (Example 6) was dissolved in 1 ml of propan-2-ol. The resulting solution was left to evaporate slowly at room temperature in a fume hood, leaving an off-white solid.

| XRPD (FIG. 11) | |
|---|---|
| 5.6(15.8) | 22.5(3.96) |
| 7.8(11.3) | 24.1(3.69) |
| 8.3(10.6) | 24.3(3.66) |
| 9.5(9.3) | 25.8(3.45) |
| 12.0(7.4) | 26.2(3.41) |
| 13.7(6.4) | 28.1(3.17) |
| 14.8(6.0) | 28.6(3.12) |
| 15.5(5.7) | |
| 16.0(5.5) | |
| 16.6(5.3) | |
| 16.8(5.3) | |
| 17.4(5.1) | |
| 20.1(4.42) | |
| 20.9(4.25) | |
| 22.1(4.03) | |

See FIG. 11, which shows the XRPD of Crystalline form of Mono Benzoate of Compound B Example 7

N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide mono fumarate Fumaric acid (168.31 mg) was added to a solution of N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide (0.84 g) in methanol (2 mL) producing an opaque mixture.

The mixture was warmed at an external temperature of 60° C. then allowed to cool to room temperature and stirred for 16 h. The title compound was obtained as an amorphous foam after evaporation to dryness.

$^1$H NMR (400 MHz, DMSO, 90° C.) δ 8.05 (m, 1H), 7.87 (m, 1H), 7.74 (m, 1H), 7.49 (m, 2H), 7.38 (m, 2H), 6.80 (m, 1H), 6.70 (m, 1H), 6.58 (s, 2H), 3.78-3.53 (m, 6H), 3.36-3.19 (m, number of protons could not be determined), 2.82-2.40 (m, number of protons could not be determined), 0.96-0.86 (m, 6H).

See FIG. 12 which shows the XRPD of Amorphous form of Mono Fumarate Salt of Compound B.

Example 8

N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide mono besylate Benzenesulfonic acid (158.51 mg) was added to a solution of N-[2-(diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide (0.58 g) in methanol (5.8 mL) producing an clear solution. The mixture was stirred at room temperature for 1 h. The title compound was obtained as an amorphous solid after evaporation to dryness.

$^1$H NMR (400 MHz, DMSO, 90° C.) δ 8.05 (d, 1H), 7.88 (d, 1H), 7.75 (m, 1H), 7.64 (m, 2H), 7.50 (m, 2H), 7.40 (m, 2H), 7.28 (m, 3H), 6.83 (m, 1H), 6.73 (m, 1H), 3.77-3.35 (m, number of protons could not be determined), 3.28 (t, 2H), 3.01-2.47 (m, number of protons could not be determined), 1.05 (br, 6H).

See FIG. 13 XRPD of Amorphous form of Mono Besylate of Compound B.

Biological Assays

Adrenergic β2 Mediated cAMP Production

Cell Preparation

H292 cells were grown in 225 cm2 flasks incubator at 37° C., 5% $CO_2$ in RPMI medium containing, 10% (v/v) FBS (foetal bovine serum) and 2 mM L-glutamine.

Experimental Method

Adherent H292 cells were removed from tissue culture flasks by treatment with Accutase™ cell detachment solution for 15 minutes. Flasks were incubated for 15 minutes in a humidified incubator at 37° C., 5% $CO_2$. Detached cells were re-suspended in RPMI media (containing 10% (v/v) FBS and 2 mM L-glutamine) at 0.05×10$^6$ cells per mL. 5000 cells in 100 μL were added to each well of a tissue-culture-treated 96-well plate and the cells incubated overnight in a humidified incubator at 37° C., 5% $CO_2$. The culture media was removed and cells were washed twice with 100 μL assay buffer and replaced with 50 μL assay buffer (HBSS solution containing 10 mM HEPES pH7.4 and 5 mM glucose). Cells were rested at room temperature for 20 minutes after which time 25 μL of rolipram (1.2 mM made up in assay buffer containing 2.4% (v/v) dimethylsulphoxide) was added. Cells were incubated with rolipram for 10 minutes after which time test compounds were added and the cells were incubated for 60 minutes at room temperature. The final rolipram concentration in the assay was 300 μM and final vehicle concentration was 1.6% (v/v) dimethylsulphoxide. The reaction was stopped by removing supernatants, washing once with 100 μL assay buffer and replacing with 50 μL lysis buffer. The cell monolayer was frozen at −80° C. for 30 minutes (or overnight).

AlphaScreen™ cAMP Detection

The concentration of cAMP (cyclic adenosine monophosphate) in the cell lysate was determined using AlphaScreen™ methodology. The frozen cell plate was thawed for 20 minutes on a plate shaker then 10 μL of the cell lysate was transferred to a 96-well white plate. 40 μL of mixed AlphaScreen™ detection beads pre-incubated with biotinylated cAMP, was added to each well and the plate incubated at room temperature for 10 hours in the dark. The AlphaScreen™ signal was measured using an EnVision spectrophotometer (Perkin-Elmer Inc.) with the recommended manufacturer's settings. cAMP concentrations were determined by reference to a calibration curve determined in the same experiment using standard cAMP concentrations. Concentration response curves for agonists were constructed and data was fitted to a four parameter logistic equation to determine both the pEC50 and Intrinsic Activity. Intrinsic Activity was expressed as a fraction relative to the maximum activity determined for formoterol in each experiment.

Selectivity Assays
Adrenergic α1D
Membrane Preparation

Membranes were prepared from human embryonic kidney 293 (HEK293) cells expressing recombinant human $\alpha1_D$ receptor. These were diluted in Assay Buffer (50 mM HEPES, 1 mM EDTA, 0.1% gelatin, pH 7.4) to provide a final concentration of membranes that gave a clear window between maximum and minimum specific binding.

Experimental Method

Assays were performed in U-bottomed 96-well polypropylene plates. 10 µL [$^3$H]-prazosin (0.3 nM final concentration) and 10 µL of test compound (10× final concentration) were added to each test well. For each assay plate 8 replicates were obtained for [$^3$H]-prazosin binding in the presence of 10 µL vehicle (10% (v/v) DMSO in Assay Buffer; defining maximum binding) or 10 µL BMY7378 (10 µM final concentration; defining non-specific binding (NSB)). Membranes were then added to achieve a final volume of 100 µL. The plates were incubated for 2 hours at room temperature and then filtered onto PEI coated GF/B filter plates, pre-soaked for 1 hour in Assay Buffer, using a 96-well plate Tomtec cell harvester. Five washes with 250 µL wash buffer (50 mM HEPES, 1 mM EDTA, pH 7.4) were performed at 4° C. to remove unbound radioactivity. The plates were dried then sealed from underneath using Packard plate sealers and MicroScint-O (50 µL) was added to each well. The plates were sealed (TopSeal A) and filter-bound radioactivity was measured with a scintillation counter (TopCount, Packard BioScience) using a 3-minute counting protocol.

Total specific binding ($B_0$) was determined by subtracting the mean NSB from the mean maximum binding. NSB values were also subtracted from values from all other wells. These data were expressed as percent of $B_0$. Compound concentration-effect curves (inhibition of [$^3$H]-prazosin binding) were determined using serial dilutions typically in the range 0.1 nM to 10 µM. Data was fitted to a four parameter logistic equation to determine the compound potency, which was expressed as pIC50 (negative log molar concentration inducing 50% inhibition of [$^3$H]-prazosin binding).

Adrenergic β1
Membrane Preparation

Membranes containing recombinant human adrenergic beta 1 receptors were obtained from Euroscreen. These were diluted in Assay Buffer (50 mM HEPES, 1 mM EDTA, 120 mM NaCl, 0.1% gelatin, pH 7.4) to provide a final concentration of membranes that gave a clear window between maximum and minimum specific binding.

Experimental Method

Assays were performed in U-bottomed 96-well polypropylene plates. 10 µL [$^{125}$I]-Iodocyanopindolol (0.036 nM final concentration) and 10 µL of test compound (10× final concentration) were added to each test well. For each assay plate 8 replicates were obtained for [$^{125}$I]-Iodocyanopindolol binding in the presence of 10 µL vehicle (10% (v/v) DMSO in Assay Buffer; defining maximum binding) or 10 µL Propranolol (10 µM final concentration; defining non-specific binding (NSB)). Membranes were then added to achieve a final volume of 100 µL. The plates were incubated for 2 hours at room temperature and then filtered onto PEI coated GF/B filter plates, pre-soaked for 1 hour in Assay Buffer, using a 96-well plate Tomtec cell harvester. Five washes with 250 µL wash buffer (50 mM HEPES, 1 mM EDTA, 120 mM NaCl, pH 7.4) were performed at 4° C. to remove unbound radioactivity. The plates were dried then sealed from underneath using Packard plate sealers and MicroScint-O (50 µL) was added to each well. The plates were sealed (TopSeal A) and filter-bound radioactivity was measured with a scintillation counter (TopCount, Packard BioScience) using a 3-minute counting protocol.

Total specific binding ($B_0$) was determined by subtracting the mean NSB from the mean maximum binding. NSB values were also subtracted from values from all other wells. These data were expressed as percent of $B_0$. Compound concentration-effect curves (inhibition of [$^{125}$I]-Iodocyanopindolol binding) were determined using serial dilutions typically in the range 0.1 nM to 10 µM. Data was fitted to a four parameter logistic equation to determine the compound potency, which was expressed as pIC$_{50}$ (negative log molar concentration inducing 50% inhibition of [$^{125}$I]-Iodocyanopindolol binding).

Dopamine D2
Membrane Preparation

Membranes containing recombinant human Dopamine Subtype D2s receptors were obtained from Perkin Elmer. These were diluted in Assay Buffer (50 mM HEPES, 1 mM EDTA, 120 mM NaCl, 0.1% gelatin, pH 7.4) to provide a final concentration of membranes that gave a clear window between maximum and minimum specific binding.

Experimental Method

Assays were performed in U-bottomed 96-well polypropylene plates. 30 µL [$^3$H]-spiperone (0.16 nM final concentration) and 30 µL of test compound (10× final concentration) were added to each test well. For each assay plate 8 replicates were obtained for [$^3$H]-spiperone binding in the presence of 30 µL vehicle (10% (v/v) DMSO in Assay Buffer; defining maximum binding) or 30 µL Haloperidol (10 µM final concentration; defining non-specific binding (NSB)). Membranes were then added to achieve a final volume of 300 µL. The plates were incubated for 2 hours at room temperature and then filtered onto PEI coated GF/B filter plates, pre-soaked for 1 hour in Assay Buffer, using a 96-well plate Tomtec cell harvester. Five washes with 250 µL wash buffer (50 mM HEPES, 1 mM EDTA, 120 mM NaCl, pH 7.4) were performed at 4° C. to remove unbound radioactivity. The plates were dried then sealed from underneath using Packard plate sealers and MicroScint-O (50 µL) was added to each well. The plates were sealed (TopSeal A) and filter-bound radioactivity was measured with a scintillation counter (TopCount, Packard BioScience) using a 3-minute counting protocol.

Total specific binding ($B_0$) was determined by subtracting the mean NSB from the mean maximum binding. NSB values were also subtracted from values from all other wells. These data were expressed as percent of $B_0$. Compound concentration-effect curves (inhibition of [$^3$H]-spiperone binding) were determined using serial dilutions typically in the range 0.1 nM to 10 µM. Data was fitted to a four parameter logistic equation to determine the compound potency, which was expressed as pIC$_{50}$ (negative log molar concentration inducing 50% inhibition of [$^3$H]-spiperone binding).

Onset Assay

Dunkin-Hartley guinea-pigs (between 200 g and 300 g on delivery) were supplied by a designated breeding establishment. The guinea-pigs were killed by cervical dislocation and the trachea removed. The adherent connective tissue was removed and each trachea cut into four rings. The tissue rings were then attached to an isometric transducer. The tissues were washed and a force of 1 g was applied to each ring. In all experiments a paired curve design was used. A priming dose of 1 µM methacholine was applied to the tissues. The tissues were then washed (three times, one minute between washes), the resting tension of 1 g was reapplied and the tissues were allowed to rest for 1 hour to equilibrate. Tissues were then contracted with 1 µM methacholine and once a steady response was obtained a cumulative concentration response curve to isoprenaline ($10^{-9}$ M-$10^{-5}$ M) was constructed. The tissues were then washed (three times, one minute between washes) and left to rest for an hour. At the end of the resting period the tissues were contracted with 1 µM methacholine and a p[A]$_{50}$ concentration of test compound added. Once the tissue had reached maximum relaxation, a 30×p[A]$_{50}$ concentration of test compound was added. Once the tissue response had reached a plateau, 10 µM sotalol was added to the bath to confirm that the relaxation was β$_2$ mediated Data were collected using the ADInstruments chart4forwindows software, which measured the maximum tension generated at each concentration of agonist.

For each concentration of the isoprenaline cumulative concentration curve, the response was calculated as % relaxation of the methacholine-induced contraction. A curve was plotted of log$_{10}$[agonist] (M) versus percentage inhibition of the methacholine-induced contraction. These data were then fitted to a non-linear regression curve fit. For each experiment, E/[A] curve data were fitted using a 4-parameter logistic function of the form:

$$E = \beta + \frac{(\beta - \alpha) \cdot [A]^m}{[A]^m + [A]_{50}^m}$$

E and [A] are the pharmacological effect (% relaxation) and concentration of the agonist respectively; α, β, [A]$_{50}$ and m are the asymptote, baseline, location and slope parameters, respectively. The p[A]$_{50}$ and IA of each isoprenaline curve was determined from this fit, to determine if the tissue was viable for generating an onset time for the test compounds.

For each p[A]$_{50}$ concentration of the test compound, the response was calculated as % relaxation of the methacholine-induced contraction. The results were plotted % relaxation against time and the time taken to reach a 90% relaxation value was calculated and recorded.

The addition of a 30×p[A]$_{50}$ concentration enabled determination of the maximum compound effect within the individual tissue. Hence, the % of the maximum compound effect at the p[A]$_{50}$ concentration was calculated and recorded.

Pharmacokinetics in the Rat

A dose solution of the test compound was prepared using a suitable dose vehicle. The concentration of the compound in the dose solution was assayed by diluting an aliquot to a nominal concentration of 50 µg·ml$^{-1}$ and calibrating against duplicate injections of a standard solution and a QC standard at this concentration. Compounds were administered intravenously as a bolus into a caudal vein to groups of three 250-350 g rats (approximately 1 ml·kg$^{-1}$). For the oral dose, a separate group of 2 or 3 animals were dosed by oral gavage (3 ml·kg$^{-1}$). Delivered doses were estimated by weight loss. Food was not usually withdrawn from animals prior to dosing, although this effect was investigated if necessary.

Blood samples (0.25 ml) were taken into 1 ml syringes from the caudal vein, transferred to EDTA tubes and plasma was prepared by centrifugation (5 min at 13000 rpm) soon after sample collection, before storage at −20° C. Typical sampling times were 2, 4, 8, 15, 30, 60, 120, 180, 240, 300 (min) or until the terminal t1/2 was accurately described.

The concentration of the analyte(s) were determined in plasma by quantitative mass spectrometry. Standard and quality control stock solutions were prepared at a concentration 1 mg/ml in methanol. A range of standard and QC stocks produced by serial dilution were added to control rat plasma (50 µl). The range of concentrations covered the range of levels of analyte present in the rat samples. Standards, QCs and samples underwent liquid extraction using 50 µl of organic solvent and 100 µl of organic solvent containing an internal standard, chosen to closely resemble the analyte. The samples were then mixed by repeated inversion, stored at −20° C. for at least 1 h, and centrifuged at 3500 rpm in a centrifuge for 20 minutes. Aliquots (120 µl) of each sample were transferred for analysis using LC-MSMS. Standard and quality control samples covering the range of concentrations found in the test samples were within 25% of the nominal concentration.

Pharmacokinetic data analysis was achieved using WinNonlin. A standard non-compartmental analysis was used to estimate the parameters such as Tmax, Cmax, Lambda_z, t1/2_Lambda_z, AUCall, AUCINF (observed), Cl(observed), Vss(observed).

The invention claimed is:

1. A pharmaceutically acceptable salt of N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide provided it is not the dihydrobromide or dihydrochloride salt.

2. A pharmaceutically acceptable salt as claimed in claim 1 wherein the salt is a trifluoroacetate, sulphate, phosphate, acetate, fumarate, maleate, citrate, pyruvate, succinate, oxalate, methanesulphonate, p-toluenesulphonate, bisulphate, benzenesulphonate, ethanesulphonate, malonate, xinafoate, ascorbate, oleate, nicotinate, saccharinate, adipate, formate, glycolate, L-lactate, D-lactate, aspartate, malate, L-tartrate, D-tartrate, stearate, 2-furoate, 3-furoate, napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), 2-mesitylenesulphonate, or 2-naphthalenesulphonate.

3. A pharmaceutically acceptable salt of N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide which is a citrate, ditosylate, phosphate, dixinafoate, sulphate, mono-benzoate, fumarate or besylate salt.

4. A pharmaceutical composition comprising a pharmaceutically acceptable salt as claimed in claim 1 in association with a pharmaceutically acceptable adjuvant, diluent or carrier.

5. A method of treating, or reducing the risk of, a disease or condition selected from adult respiratory distress syndrome (ARDS), pulmonary emphysema, bronchitis, bronchiectasis, chronic obstructive pulmonary disease (COPD), asthma and rhinitis which comprises administering to a patient in need thereof an effective amount of a pharmaceutically acceptable salt as claimed in claim 1.

* * * * *